(12) United States Patent
Ware et al.

(10) Patent No.: US 10,961,297 B2
(45) Date of Patent: Mar. 30, 2021

(54) BTLA FUSION PROTEIN AGONISTS AND USES THEREOF

(71) Applicants: Sanford Burnham Prebys Medical Discovery Institute, La Jolla, CA (US); Pfizer Inc., New York, NY (US)

(72) Inventors: Carl F. Ware, La Jolla, CA (US); John Sedy, La Jolla, CA (US); Tigran Aivazian, San Diego, CA (US); Brian Miller, San Diego, CA (US); Natasha K. Crellin, San Carlos, CA (US)

(73) Assignees: SANFORD BURNHAM PREBYS MEDICAL DISCOVERY INSTITUTE, La Jolla, CA (US); PFIZER INC., New York, NY (US)

( * ) Notice: Subject to any disclaimer, the term of this patent is extended or adjusted under 35 U.S.C. 154(b) by 158 days.

(21) Appl. No.: 15/737,259

(22) PCT Filed: Jun. 29, 2016

(86) PCT No.: PCT/US2016/040108
§ 371 (c)(1),
(2) Date: Dec. 15, 2017

(87) PCT Pub. No.: WO2017/004213
PCT Pub. Date: Jan. 5, 2017

(65) Prior Publication Data
US 2018/0170999 A1 Jun. 21, 2018

Related U.S. Application Data

(60) Provisional application No. 62/187,105, filed on Jun. 30, 2015.

(51) Int. Cl.
*A61K 38/17* (2006.01)
*C07K 14/715* (2006.01)
*C07K 14/71* (2006.01)
*A61K 45/06* (2006.01)
*C07K 14/705* (2006.01)
*A61K 38/00* (2006.01)

(52) U.S. Cl.
CPC ............. *C07K 14/71* (2013.01); *A61K 38/17* (2013.01); *A61K 38/177* (2013.01); *A61K 38/1793* (2013.01); *A61K 45/06* (2013.01); *C07K 14/70578* (2013.01); *C07K 14/70596* (2013.01); *A61K 38/00* (2013.01); *C07K 2319/30* (2013.01)

(58) Field of Classification Search
CPC .............. A61K 38/177; A61K 38/1793; C07K 2319/30; C07K 14/705; C07K 14/70575; C07K 14/71; C07K 19/00
See application file for complete search history.

(56) References Cited

U.S. PATENT DOCUMENTS

| 6,291,207 B1 * | 9/2001 | Spear .................... C07K 14/71 435/252.3 |
| 2009/0311280 A1 | 12/2009 | Cheung et al. |
| 2010/0104559 A1 * | 4/2010 | Ware .................. C07K 16/2818 514/1.1 |
| 2010/0129389 A1 * | 5/2010 | Ware .................. C07K 16/2803 424/185.1 |
| 2013/0164306 A1 | 6/2013 | Ware |
| 2014/0220051 A1 | 8/2014 | Ware et al. |

FOREIGN PATENT DOCUMENTS

| CN | 102762593 A | 10/2012 |
| CN | 107474136 A | 12/2017 |
| WO | WO 2006/054961 A2 | 5/2006 |
| WO | WO 2006/063067 A2 | 6/2006 |
| WO | WO 2013/074738 A1 | 5/2013 |
| WO | WO-2017004213 A1 | 1/2017 |

OTHER PUBLICATIONS

Sedy et al. A herpesvirus entry mediator mutein with selective agonist action for the inhibitory receptor B and T lymphocyte attenuator. J Biol Chem 292(51): 21060-21070, 2017.*
Cheung, Timothy C. et al.: "*Evolutionarily divergent herpesviruses modulate T cell activation by targeting the herpesvirus entry mediator cosignaling pathway.*"; Proceedings of the National Academy of Sciences of the United States of America, Sep. 13, 2005, vol. 102, Nr. 37, pp. 13218-13223.
Compaan, Deanne M. et al: "*Attenuating Lymphocyte Activity: The Crystal Structure of the BTLA-HVEM Complex*"; Journal of Biological Chemistry, vol. 280, No. 47, Nov. 25, 2005, pp. 39553-39561, XP055538860.
Extended European Search Report dated Feb. 14, 2019, regarding EP 16 818 691.4.
Gonzalez, L. C. et al.: "*A coreceptor interaction between the CD28 and TNF receptor family members B and T lymphocyte attenuator and herpesvirus entry mediator*"; Proceedings of the National Academy of Sciences of the United States of America, vol. 102, No. 4, Jan. 25, 2005, pp. 1116-1121, XP055539458.
Kojima, Rieko et al.: "*Molecular Basis for Herpesvirus Entry Mediator Recognition by the Human Immune Inhibitory Receptor CD160 and Its Relationship to the Cosignaling Molecules BTLA and LIGHT*"; Journal of Molecular Biology, Academic Press, UK, vol. 413, No. 4, Sep. 13, 2011, pp. 762-772, XP028326146.
Murphy, Kenneth M. et al.: "*Balancing co-stimulation and inhibition with BTLA and HVEM*"; Nature Reviews Immunology, vol. 61,2, No. 9, Sep. 1, 2006, pp. 671-681, XP055333412.

(Continued)

*Primary Examiner* — Bridget E Bunner
(74) *Attorney, Agent, or Firm* — Wilson Sonsini Goodrich & Rosati

(57) ABSTRACT

The present invention is based on the seminal discovery that BTLA agonist fusion proteins modulate an immune response. Specifically, the present invention provides fusion proteins that bind BTLA enhancing BTLA signaling. The present invention further provides methods of treating cancer and immune and inflammatory diseases and disorders with a BTLA agonist fusion protein as described herein.

5 Claims, 19 Drawing Sheets

Specification includes a Sequence Listing.

(56) References Cited

OTHER PUBLICATIONS

Pasero, Christine et al.: "*The HVEM network: new directions in targeting novel costimulatory/co-inhibitory molecules for cancer therapy.*"; Current Opinion in Pharmacology, Aug. 2012, vol. 12, Nr, 4, pp. 478-485.AK.
Sedy, John et al.: "*Tumor Necrosis Factor Superfamily in Innate Immunity and Inflammation*"; Cold Spring Harbor Perspectives in Biology, 2015, vol. 7, No. 4, 19 pages, a016279, XP055538835.
PCT/US2016/040108 International Search Report and Written Opinion dated Nov. 1, 2016.
Sedy et al. CD160 Activation by Herpesvirus Entry Mediator Augments Inflammatory Cytokine Production and Cytolytic Function by NK Cells. J Immunol 191(2):828-836 (2013).
Croft et al., "TNF Superfamily in Inflammatory Disease: Translating Basic Insights," *Trends Immunol.* (2012), 33(3):144-152, Elsevier Ltd..
Pierer et al., "Herpesvirus Entry Mediator-Ig Treatment during Immunization Aggravates Rheumatoid Arthritis in the Collagen-Induced Arthritis Model," *J. Immunol.* (2009), 182:3139-3145, The American Association of Immunologists, Inc.

\* cited by examiner

```
   1 gccgcagcaa tggcgctgag ttcctctgct ggagttcatc ctgctagctg ggttcccgag
  61 ctgccggtct gagcctgagg catggagcct cctggagact gggggcctcc tccctggaga
 121 tccaccccca gaaccgacgt cttgaggctg gtgctgtatc tcaccttcct gggagccccc
 181 tgctacgccc cagctctgcc gtcctgcaag gaggacgagt acccagtggg ctccgagtgc
 241 tgccccaagt gcagtccagg ttatcgtgtg aaggaggcct gcggggagct gacgggcaca
 301 gtgtgtgaac cctgccctcc aggcacctac attgcccacc tcaatggcct aagcaagtgt
 361 ctgcagtgcc aaatgtgtga cccagccatg ggcctgcgcg cgagccggaa ctgctccagg
 421 acagagaacg ccgtgtgtgg ctgcagccca ggccacttct gcatcgtcca ggacggggac
 481 cactgcgccg cgtgccgcgc ttacgccacc tccagcccgg ccagagggt gcagaaggga
 541 ggcaccgaga gtcaggacac cctgtgtcag aactgccccc cggggacctt ctctcccaat
 601 gggaccctgg aggaatgtca gcaccagacc aagtgcagct ggctggtgac gaaggccgga
 661 gctgggacca gcagctccca ctgggtatgg tggtttctct cagggagcct cgtcatcgtc
 721 attgtttgct ccacagttgg cctaatcata tgtgtgaaaa gaagaaagcc aagggtgat
 781 gtagtcaagg tgatcgtctc cgtccagcgg aaaagacagg aggcagaagg tgaggccaca
 841 gtcattgagg ccctgcaggc ccctccggac gtcaccacgg tggccgtgga ggagacaata
 901 ccctcattca cggggaggag cccaaaccac tgacccacag actctgcacc ccgacgccag
 961 agatacctgg agcgacggct gctgaaagag gctgtccacc tggcgaaacc accggagccc
1021 ggaggcttgg gggctccgcc ctgggctgg
```

FIG. 19A

```
   1 MEPPGDWGPP PWRSTPRTDV LRLVLYLTFL GAPCYAPALP SCKEDEYPVG SECCPKCSPG
  61 YRVKEACGEL TGTVCEPCPP GTYIAHLNGL SKCLQCQMCD PAMGLRASRN CSRTENAVCG
 121 CSPGHFCIVQ DGDHCAACRA YATSSPGQRV QKGGTESQDT LCQNCPPGTF SPNGTLEECQ
 181 HQTKCSWLVT KAGAGTSSSH WVWWFLSGSL VIVIVCSTVG LIICVKRRKP RGDVVKVIVS
 241 VQRKRQEAEG EATVIEALQA PPDVTTVAVE ETIPSFTGRS PNH
```

BTLA FUSION PROTEIN AGONISTS AND USES THEREOF

CROSS-REFERENCE TO RELATED APPLICATIONS

This application is a 35 USC § 371 National Stage application of International Application No. PCT/US2016/040108 filed Jun. 29, 2016; which claims the benefit under 35 USC § 119(e) to U.S. Application Ser. No. 62/187,105 filed Jun. 30, 2015. The disclosure of each of the prior applications is considered part of and is incorporated by reference in the disclosure of this application.

GOVERNMENT SUPPORT

This invention was made in part with government support under Grant No. R01CA164679 awarded by the National Institutes of Health. The United States government has certain rights in this invention.

INCORPORATION OF SEQUENCE LISTING

The material in the accompanying sequence listing is hereby incorporated by reference into this application. The accompanying sequence listing text file, name 42256-821_831_SL.txt, was created on Mar. 18, 2020, and is 23,422 bytes in size. The file can be assessed using Microsoft Word on a computer that uses Windows OS.

FIELD OF THE INVENTION

The present invention relates generally to fusion proteins and more specifically to the development and of use of BTLA agonist fusion proteins and uses thereof to modulate immune response and treat diseases and disorders.

BACKGROUND OF THE INVENTION

The tumor necrosis factor (TNF) receptor herpesvirus entry mediator (HVEM; TNFRSF14) is a focal point for manipulation by viral pathogens, and mutation in cancers and autoimmunity. In humans, HVEM interacts with the TNF superfamily cytokines, LIGHT and Lymphotoxin α, and the immunoglobulin (Ig) family containing receptors B and T Lymphocyte Attenuator (BTLA) and CD160. Membrane associated LIGHT, BTLA, and CD160, all activate NF-κB signaling downstream of HVEM following receptor engagement, while HVEM activates the receptors BTLA and CD160 resulting in bi-directional signaling between neighbor cells. Cells co-expressing HVEM and BTLA or CD160 can also form cell-intrinsic complexes of these proteins that prevent accessibility of these receptors to extracellular ligands due to steric hindrance.

BTLA mediated inhibition has been shown to regulate a number of different cellular pathways, including antigen receptor signaling in T and B cells. In T cells, BTLA was first shown to engage inhibitory signaling pathways including the activation of SH2-domain-containing protein tyrosine phosphatases (SHP)-1 and 2. Recently BTLA has been shown to regulate toll-like receptor signaling in dendritic cells, and IL-7 signaling in γδ T cells. However, in human natural killer (NK) cells HVEM can also promote cytolytic and pro-inflammatory pathways through CD160 as a host counter measure to human cytomegalovirus (HCMV). Additionally, recent work describing CD160-deficiency in mice confirms its pro-inflammatory function in NK cells.

There is a large unmet need for novel therapies designed to inhibit lymphocyte activity In patients suffering from immune mediated pathology such as in graft versus host disease or autoimmune diseases. In many types of these diseases there is a limited array of approved treatments, or some individuals fail to respond to available treatments. An attractive target for novel therapies is agonistic activation of inhibitory receptors expressed by pathogenic lymphocytes that are the cause of autoimmune disease. Attempts to develop antibody-based therapy designed to activate human inhibitory receptors have largely met with failure despite promising results in animal models.

SUMMARY OF THE INVENTION

The present invention is based on the seminal discovery that BTLA agonist fusion proteins modulate an immune response. Specifically, the present invention provides fusion proteins that bind BTLA enhancing BTLA signaling. The present invention further provides methods of treating cancer and immune and inflammatory diseases and disorders with a BTLA agonist fusion protein as described herein.

In one embodiment, the present invention provides a fusion protein including a non-naturally occurring HVEM protein and an Fc protein, wherein the fusion protein includes an extracellular domain of the HVEM protein and an Fc protein. In one aspect, the fusion protein is a BTLA agonist. In another aspect, the fusion protein includes at least one mutation in the HVEM protein. In an additional aspect, the mutation is S58R, S58K, S58Q, G68T, L70D, L70E, L70N, L70W, L90A or a combination thereof. In one aspect, the fusion protein further includes at least one mutation in the HVEM protein, for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A. In one aspect, the Fc protein is IgA, IgG, IgD, IgE or IgM. In another aspect, the Fc protein is IgG1, IgG2, IgG3 or IgG4. In a specific aspect, the IgG Fc protein is human.

In an additional embodiment, the present invention provides a pharmaceutical composition including a fusion protein such as a non-naturally occurring HVEM protein and an Fc protein and a pharmaceutically acceptable carrier. In one aspect, the fusion protein is a BTLA agonist. In another aspect, the fusion protein includes an extracellular domain of the HVEM protein and an Fc protein. In another aspect, the fusion protein includes at least one mutation in the HVEM protein. In an additional aspect, the mutation is S58R, S58K, S58Q, G68T, L70D, L70E, L70N, L70W, L90A or a combination thereof. In an additional aspect, the fusion protein further includes at least one mutation in the HVEM protein for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E;

L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A. In one aspect, the Fc protein is IgA, IgG, IgD, IgE or IgM. In another aspect, the Fc protein is IgG1, IgG2, IgG3 or IgG4. In a specific aspect, the IgG Fc protein is human.

In one embodiment, the present invention provides a method of treating a BTLA related disorder including administering a fusion protein such as a non-naturally occurring HVEM protein and an Fc protein to a subject in need thereof, thereby treating the BTLA related disorder. In one aspect, the BTLA related disorder is cancer or an autoimmune disease or disorder. In an additional aspect, the autoimmune disease or disorder is Addison's disease, amyotrophic lateral sclerosis, Crohn's disease, Cushing's Syndrome, diabetes mellitus type 1, graft versus host disease, Graves' disease, Guillain-Barré syndrome, lupus erythematosus, multiple sclerosis, psoriasis, psoriatic arthritis, rheumatoid arthritis, sarcoidosis, scleroderma, systemic lupus erythematosus, transplant rejection, or vasculitis. In another aspect, the cancer is prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract. In a further aspect, BTLA signaling is increased. In another aspect, the fusion protein is a BTLA agonist.

In one aspect, the fusion protein includes an extracellular domain of the HVEM protein and an Fc protein. In an additional aspect, the fusion protein includes amino acid residues 39-161 of SEQ ID NO:2 and an Fc protein. In a further aspect, the Fc protein is IgA, IgG, IgD, IgE or IgM. In certain aspects, the Fc protein is IgG1, IgG2, IgG3 or IgG4. In a specific aspect, the IgG Fc protein is human. In one aspect, the fusion protein includes at least one mutation in the HVEM protein. In an additional aspect, the mutation is S58R, S58K, S58Q, G68T, L70D, L70E, L70N, L70W, L90A or a combination thereof. In one aspect, the fusion protein further includes at least one mutation in the HVEM protein, for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A.

In one aspect, the method also includes administering an immune response modulator or chemotherapeutic agent. In another aspect, the immune response modulator is eicosanoids, cytokines, prostaglandins, interleukins, chemokines, check point regulators, TNF superfamily members, TNF receptor superfamily members and/or interferons. In an additional aspect, the immune response modulator is CXCL-8, CCL2, CCL3, CCL4, CCL5, CCL11, CXCL10, IL1, IL2, IL3, IL4, IL5, IL6, IL7, IL8, IL9, IL10, IL11, IL12, IL13, IL15, IL17, IL17, IFN-α, IFN-β, IFN-ε, IFN-γ G-CSF, TNF-α, CTLA4, CD20, PD1, PD1L1, PD1L2, ICOS, CD200, CD52, LTα, LTαβ, LIGHT, CD27L, 41BBL, FasL, Ox40L, April, TL1A, CD30L, TRAIL, RANKL, BAFF, TWEAK, CD40L, EDA1, EDA2, APP, NGF, TNFR1, TNFR2, LTβR, HVEM, CD27, 4-1BB, Fas, Ox40, AITR, DR3, CD30, TRAIL-R1, TRAIL-R2, TRAIL-R3, TRAIL-R4, RANK, BAFFR, TACI, BCMA, Fn14, CD40, EDAR XEDAR, DR6, DcR3, NGFR-p75, and/or Taj. In a certain aspects, the immune response modulator is tocilizumab (Actemra), CDP870 (Cimzia), enteracept (Enbrel), adalimumab (Humira), Kineret, abatacept (Orencia), infliximab (Remicade), rituximab (Rituxan), golimumab (Simponi), Avonex, Rebif, ReciGen, Plegridy, Betaseron, Copaxone, Novatrone, natalizumab (Tysabri), fingolimod (Gilenya), teriflunomide (Aubagio), BG12, Tecfidera, and/or alemtuzumab (Campath, Lemtrada).

In a further aspect, the chemotherapeutic agent is Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (dacliximab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, and/or natalizumab. In one aspect, phosphorylation of ERK1/2 and/or ZAP70/Syk is reduced. In another aspect, total cellular phosphorylation and phosphorylation of SHP2 is induced.

In a further embodiment, the present invention provides a method of modulating an immune response in a subject including administering a fusion protein such as a non-naturally occurring HVEM protein and an Fc protein to the subject, thereby modulating the immune response. In one aspect, the fusion protein is a BTLA agonist. In another aspect, the fusion protein includes the extracellular domain of the HVEM protein and an Fc protein. In another aspect, the fusion protein includes at least one mutation in the HVEM protein. In an additional aspect, the mutation is S58R, S58K, S58Q, G68T, L70D, L70E, L70N, L70W, L90A or a combination thereof. In an additional aspect, the fusion protein further includes at least one mutation in the HVEM protein, for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A. In one aspect, the Fc protein is IgA, IgG, IgD, IgE or IgM. In another aspect, the Fc protein is IgG1, IgG2, IgG3 or IgG4. In a specific aspect, the IgG Fc protein is human. In one aspect, BTLA signaling is increased. In another aspect, phosphorylation of ERK1/2 and/or ZAP70/Syk is reduced. In an additional aspect, total cellular phosphorylation and phosphorylation of SHP2 is induced. In a further aspect, the subject has a BTLA related disease or disorder. In certain aspects, the BTLA related disease is cancer or an autoimmune disease or disorder.

In one embodiment, the present invention provides a method of modulating BTLA signaling in a cell, including contacting a BTLA expressing cell with a fusion protein such as a non-naturally occurring HVEM protein and an Fc protein, thereby modulating BTLA signaling. In one the BTLA signaling is increased. In another aspect, the fusion protein includes an extracellular domain of the HVEM protein and an Fc protein. In another aspect, the fusion protein includes at least one mutation in the HVEM protein. In an additional aspect, the mutation is S58R, S58K, S58Q, G68T, L70D, L70E, L70N, L70W, L90A or a combination thereof. In an additional aspect, the fusion protein further includes at least one mutation in the HVEM protein, for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R, L70D and L90A; S58R and G68T; S58R and L70W; S58R, G68T and L90A; S58R, L70W and L90A; S58R, G68T, L70D and L90A; or S58R, G68T, L70W and L90A. In one aspect, the Fc protein is IgA, IgG, IgD, IgE or IgM. In another aspect, the Fc protein is IgG1, IgG2, IgG3 or IgG4. In a specific aspect, the IgG Fc protein is human. In one aspect, phosphorylation of ERK1/2 and/or ZAP70/Syk is reduced. In another aspect, total cellular phosphorylation and phosphorylation of SHP2 is induced.

BRIEF DESCRIPTION OF THE DRAWINGS

FIG. 1A shows images of human CMV UL144 indicating mutated surface residues. FIG. 1B shows binding curves for the indicated UL144 mutants. FIG. 1C shows the $K_d$ of BTLA-Fc binding to UL144 proteins.

FIG. 2A shows images of human HVEM indicating mutated surface residues. FIG. 2B shows HVEM binding in cells transduced with LIGHT. FIG. 2C shows HVEM binding in cells transduced with BTLA-Fc. FIG. 2D shows HVEM binding in cells transduced with CD160-Fc. FIG. 2E shows the $K_d$ of LIGHT binding to HVEM mutant proteins. FIG. 2F shows the $K_d$ of BTLA-Fc binding to HVEM mutant proteins. FIG. 2G shows the $K_d$ of CD160-Fc binding to HVEM mutant proteins. FIG. 2H shows an array of individual DLBCL biopsies with each column representing one DLBCL sample.

FIG. 3A shows two images of BTLA. FIG. 3B shows representative traces following injection of human HVEM-Fc. FIG. 3C shows representative traces following injection of human CMV UL144-Fc. FIG. 3D shows BJAB cells transduced with BTLA were incubated with anti-BTLA and then stained with HVEM-Fc. FIG. 3E shows BJAB cells transduced with BTLA, incubated with anti-BTLA and then stained with human CMV UL144-Fc.

FIGS. 4A-C show JTAg cells transduced with the indicated HVEM ligands and cultured with microspheres coupled to anti-CD3 with or without Fc proteins. FIG. 4A shows the cells stained for phospho-ERK1/2 (T202/Y204). FIG. 4B shows the cells stained for phospho-ZAP70/Syk (Y319/Y352). FIG. 4C shows the cells stained for phospho-tyrosine.

FIG. 5A shows Western blots of whole cell extracts of phospho-JAK1, phospho-STAT5, and actin. FIG. 5B are graphs showing the quantitation of band intensity normalized to actin.

FIGS. 6A-C show JTAg cells transduced with HVEM ligands cultured with microspheres coupled to anti-CD3 with or without Fc proteins. FIG. 6A shows staining for phospho-ERK1/2 (T202/Y204). FIG. 6B shows staining for phospho-ZAP70/Syk (Y319/Y352). FIG. 6C shows staining for phospho-SHP2 (Y542).

FIG. 7A shows the extracellular domains of human HVEM (SEQ ID NO: 92) and human CMV UL144 (SEQ ID NO: 93). FIG. 7A also discloses the RhCMV UL144 sequence as SEQ ID NO: 94 and the consensus sequence as SEQ ID NO: 95. FIG. 7B shows histograms of 293T cells transduced with wild-type or mutated human CMV UL144 stained with anti-UL144 (2F11). FIG. 7C shows 293T cells transduced with wild-type or mutated human CMV UL144 or with HVEM stained with LIGHT. FIG. 7D shows 293T cells transduced with wild-type or mutated human CMV UL144 or with HVEM stained with BTLA-Fc. FIG. 7E shows 293T cells transduced with wild-type or mutated human CMV UL144 or with HVEM stained with CD160-Fc.

FIG. 8A shows a summary of TNFRSF14 mutations (dots) observed in human FL and DLBCL biopsies. FIG. 8B shows 293T cells transduced with wild-type or mutated human HVEM stained with anti-HVEM.

FIG. 9A shows specific MFI staining of 6F4, J168, or M1H26 with anti-BTLA. FIG. 9B shows specific MFI staining with HVEM-Fc or UL144-Fc. FIG. 9C shows 293T cells transfected with BTLA alone or together with HVEM or human CMV UL144 stained with HVEM-Fc. FIG. 9D shows 293T cells transfected with BTLA alone or together with HVEM or human CMV UL144 stained with CMV UL144-Fc. FIG. 9E shows 293T cells transfected with HVEM stained with BTLA-Fc. FIG. 9F shows 293T cells transfected with HVEM human CMV UL144 stained with BTLA-Fc.

FIG. 10A shows JTAg cells transduced with the indicated HVEM ligands or control vector stained with anti-human BTLA (top), anti-human CD160 (middle), or HVEM-Fc followed by species specific secondary (bottom). FIG. 10B shows BJAB cells cultured with microspheres coupled to anti-IgM with or without titrated Fc proteins prior to intracellular staining.

FIGS. 11 A-C show selective BTLA agonists inhibit IL-2 signaling.

FIGS. 12 A-B show that de novo mutant HVEM inhibits ZAP70/Syk activation. FIG. 12A shows staining for phospho-NF-κB. FIG. 12B shows staining for phospho-tyrosine.

FIGS. 13 A-G show that diverse pathogen-associated and de novo bioengineered HVEM mutein BTLA agonists inhibit T cell signaling. JTAg cells transduced with the indicated HVEM ligands were cultured with microspheres coupled to anti-CD3 with or without Fc proteins.

FIG. 14A shows culturing for 10 minutes. FIG. 14B shows culturing for 60 minutes.

FIG. 15A shows HVEM-Fc coupled microspheres. FIG. 15B shows UL144 Fc coupled microspheres. FIG. 15C shows $HVEM^{R109w}$ Fc coupled microspheres. FIG. 15D shows $HVEM^{RTWA}$ Fc coupled microspheres.

FIG. 16A shows Western blots of whole cell extracts of phospho-JAK1, phospho-STAT5, and actin. FIG. 16B shows graphs of quantitation of band intensity normalized to actin.

FIG. 17A shows cells transfected with CD160. FIG. 17B shows cells transfected with mouse BTLA. FIG. 17C shows cells transfected with mouse LIGHT.

FIG. 18A shows histological analysis. FIGS. 18B-C show epidermal thickening.

FIGS. 19A-B show the nucleic acid and amino acid sequences for human HVEM. FIG. 19A shows the nucleic acid sequence for human HVEM (SEQ ID NO: 1). FIG. 19B shows the amino acid sequence for human HVEM (SEQ ID NO: 2).

DETAILED DESCRIPTION OF THE INVENTION

Figures 1A, 1B, 1C:
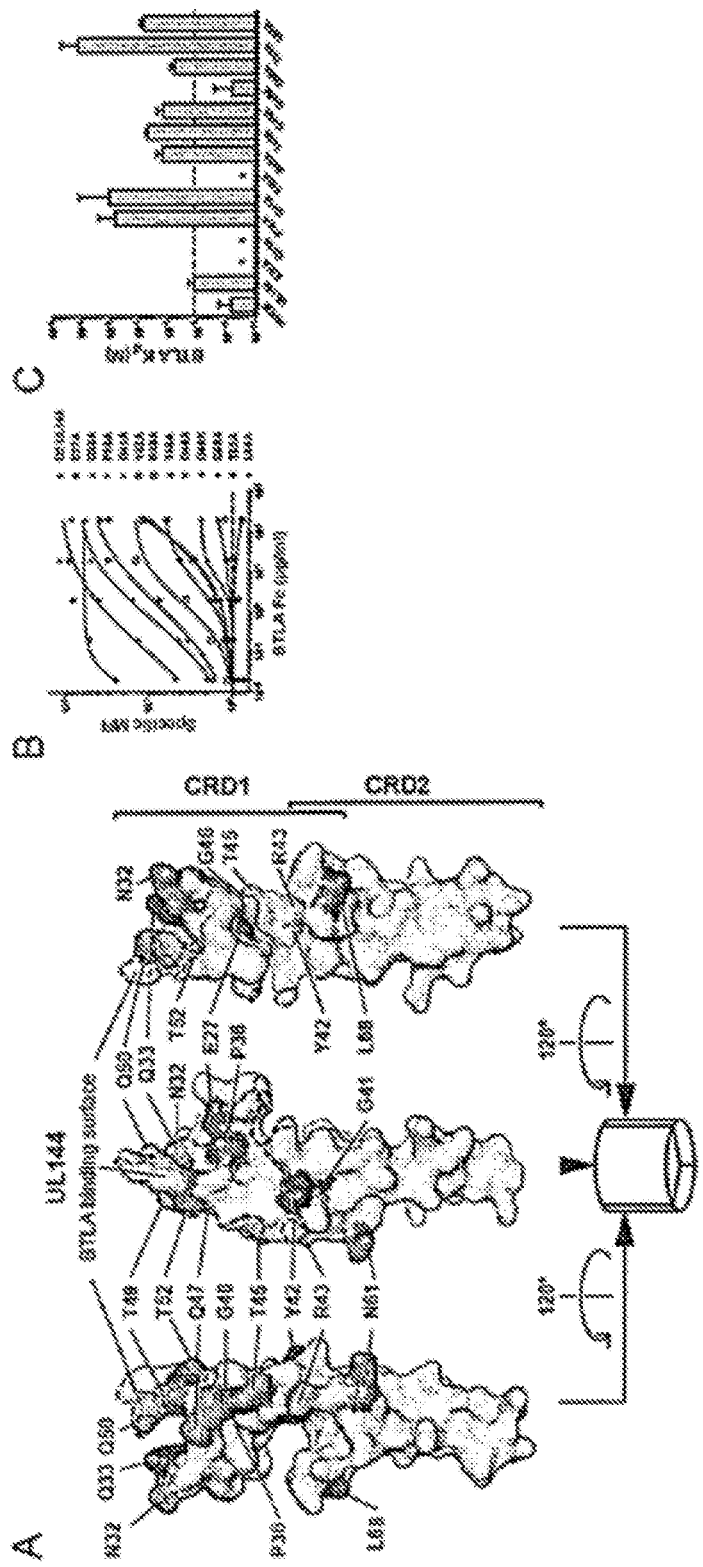
FIGS. 1A-C show the identification of the BTLA binding surface of UL144.

The present invention is based on the seminal discovery that BTLA agonist fusion proteins modulate an immune response. Specifically, the present invention provides fusion proteins that bind BTLA enhancing BTLA signaling. The present invention further provides methods of treating cancer and immune and inflammatory diseases and disorders with a BTLA agonist fusion protein as described herein.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The definitions set forth below are for understanding of the disclosure but shall in no way be considered to supplant the understanding of the terms held by those of ordinary skill in the art.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. Each variable region is includes three segments called complementarity-determining regions (CDRs) or hypervariable regions and a more highly conserved portions of variable domains are called the framework region (FR). The variable domains of heavy and light chains each includes four FR regions, largely adopting a β-sheet configuration, connected by three CDRs, which form loops connecting, and in some cases forming part of the β-sheet structure. The CDRs in each chain are held together in close proximity by the FRs and, with the CDRs from the other chain, contribute to the formation of the antigen-binding site of antibodies. The constant domains are not involved directly in binding an antibody to an antigen, but exhibit various effector functions, such as participation of the antibody in antibody dependent cellular cytotoxicity.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The Fc region of an antibody is the tail region of an antibody that interacts with cell surface receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains (CH domains 2-4) in each polypeptide chain. The Fc regions of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues.

The term "antibody" as used herein refers to intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" include a portion of an intact antibody, preferably the antigen binding or variable region of the intact antibody. Examples of antibody fragments include Fc, Fab, Fab', F(ab')$_2$, and Fv fragments; diabodies, tribodies and the like; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies including the population are identical except for possible naturally occurring mutations that may be present in minor amounts. Monoclonal antibodies are highly specific, being directed against a single antigenic site. Furthermore each monoclonal antibody is directed against a single determinant on the antigen. In addition to their specificity, the monoclonal antibodies are advantageous in that they are synthesized by the hybridoma culture, uncontaminated by other immunoglobulins. For example, the monoclonal antibodies to be used in accordance with the present invention may be made by hybridomas, by recombinant DNA methods or isolated from phage antibody libraries.

The terms "fusion molecule" and "fusion protein" are used interchangeably and are meant to refer to a biologically active polypeptide, e.g., a HVEM or antibody or fragment thereof (e.g., Fc region), with or without a further effector molecule usually a protein or peptide sequence covalently linked (i.e. fused) by recombinant, chemical or other suitable method. If desired, the fusion molecule can be fused at one or several sites through a peptide linker sequence. Alternatively, the peptide linker may be used to assist in construction of the fusion molecule. Specifically preferred fusion molecules are fusion proteins. Generally fusion molecule also can include conjugate molecules.

Fc-Fusion proteins (also known as Fc chimeric fusion protein, Fc-Ig, Ig-based Chimeric Fusion protein and Fc-tag protein) are composed of the Fc domain of IgG genetically linked to a peptide or protein of interest. Fc-Fusion proteins have become valuable reagents for in vivo and in vitro research.

The Fc-fused binding partner can range from a single peptide, a ligand that activates upon binding with a cell surface receptor, signaling molecules, the extracellular domain of a receptor that is activated upon dimerization or as a bait protein that is used to identify binding partners in a protein microarray.

One of the most valuable features of the Fc domain in vivo, is it can dramatically prolong the plasma half-life of the protein of interest, which for bio-therapeutic drugs, results in an improved therapeutic efficacy; an attribute that has made Fc-Fusion proteins attractive bio-therapeutic agents.

The Fc fusion protein may be part of a pharmaceutical composition including an Fc fusion protein and a pharmaceutically acceptable carrier excipients or carrier. Pharmaceutically acceptable carriers, excipients or stabilizers are well known in the art (Remington's Pharmaceutical Sciences, 16th edition, Osol, A. Ed. (1980)). Acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG).

As used herein, the term "modulating an immune response" refers to either enhancing or inhibiting an immune response. In some aspects, the fusion proteins of the present invention inhibit or reduce an immune response.

As used herein, the term "modulating BTLA signaling" refers to either increasing or decreasing BTLA signaling. In some aspects, the fusion proteins of the present invention increase BTLA signaling.

As used herein, the terms "treating" or "treatment" or "alleviation" refer to therapeutic treatment, prophylactic and/or preventative measures, wherein the object is to prevent or slow down (lessen) the targeted pathologic condition or disorder. Those in need of treatment include those already with the disorder as well as those prone to have the disorder or those in whom the disorder is to be prevented.

The term "therapeutic agent" as used herein includes a chemical compound or composition capable of inducing a desired therapeutic effect when administered to a patient or subject. An example of a therapeutic agent of the present invention is a BTLA agonist fusion protein.

As used herein, the terms "effective amount" or "therapeutically effective amount" of a drug used to treat a disease is an amount that can reduce the severity of a disease, reduce the severity of one or more symptoms associated with the disease or its treatment, or delay the onset of more serious symptoms or a more serious disease that can occur with some frequency following the treated condition. An "effective amount" may be determined empirically and in a routine manner, in relation to the stated purpose.

The therapeutic agent may be administered by any suitable means, including topical, parenteral, subcutaneous, intraperitoneal, intrapulmonary, intranasal, intravenous, and/ or intralesional administration in order to treat the subject. However, in exemplary embodiments, the therapeutic agent is formulated for topical application, such as in the form of a liquid, cream, gel, ointment, foam spray or the like As used herein the terms "BTLA related disorder" or "BTLA related disease" refer to any condition that would benefit from treatment with a BTLA agonist fusion protein. Examples of diseases and disorders that would benefit from a BTLA agonist fusion protein treatment include cancer, immune, autoimmune and inflammatory diseases and disorders.

An immune disease or disorder is a dysfunction of the immune system. These disorders can be characterized in several different ways: by the component(s) of the immune system affected; by whether the immune system is overactive or underactive and by whether the condition is congenital or acquired. Autoimmune diseases arise from an abnormal immune response of the body against substances and tissues normally present in the body (autoimmunity). A major understanding of the underlying pathophysiology of autoimmune diseases has been the application of genome wide association scans that have identified a striking degree of genetic sharing among the autoimmune diseases.

Autoimmune disorders include, but are not limited to, Acute disseminated encephalomyelitis (ADEM), Addison's disease, Agammaglobulinemia, Alopecia areata, Amyotrophic lateral sclerosis (aka Lou Gehrig's disease), Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, graft versus host disease, Graves' disease, Guillain-Barré syndrome, Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease, Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Ménière's disease, Narcolepsy, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome, Schnitzler syndrome, Scleritis, Scleroderma, Serum Sickness, Sjögren's syndrome, Spondyloarthropathy, Stiff person syndrome, Still's disease, Subacute bacterial endocarditis (SBE), Susac's syndrome, Sweet's syndrome, Sydenham chorea, Sympathetic ophthalmia, Systemic lupus erythematosus, Takayasu's arteritis, Temporal arteritis, Thrombocytopenia, Tolosa-Hunt syndrome, Transverse myelitis, Ulcerative colitis, Undifferentiated spondyloarthropathy, Urticarial vasculitis, Vasculitis, Vitiligo, Wegener's granulomatosis.

The term "immune modulator" as used herein refers to any therapeutic agent that modulates the immune system. Examples of immune modulators include eicosanoids, cytokines, prostaglandins, interleukins, chemokines, checkpoint regulators, TNF superfamily members, TNF receptor superfamily members and interferons. Specific examples of immune modulators include PGI2, PGE2, PGF2, CCL14, CCL19, CCL20, CCL21, CCL25, CCL27, CXCL12, CXCL13, CXCL-8, CCL2, CCL3, CCL4, CCL5, CCL11, CXCL10, IL1, IL2, IL3, IL4, IL5, IL6, IL7, IL8, IL9, IL10, IL11, IL12, IL13, IL15, IL17, IL17, INF-α, INF-β, INF-ε, INF-γ, G-CSF, TNF-α, CTLA, CD20, PD1, PD1L1, PD1L2, ICOS, CD200, CD52, LTα, LTαε, LIGHT, CD27L, 41BBL, FasL, Ox40L, April, TL1A, CD30L, TRAIL, RANKL, BAFF, TWEAK, CD40L, EDA1, EDA2, APP, NGF, TNFR1, TNFR2, LTβR, HVEM, CD27, 4-1BB, Fas, Ox40, AITR, DR3, CD30, TRAIL-R1, TRAIL-R2, TRAIL-R3, TRAIL-R4, RANK, BAFFR, TACI, BCMA, Fn14, CD40, EDAR XEDAR, DR6, DcR3, NGFR-p75, and Taj. Other examples of immune modulators include tocilizumab (Actemra), CDP870 (Cimzia), enteracept (Enbrel), adalimumab (Humira), Kineret, abatacept (Orencia), infliximab (Remicade), rituximab (Rituxan), golimumab (Simponi), Avonex, Rebif, ReciGen, Plegridy, Betaseron, Copaxone, Novatrone, natalizumab (Tysabri), fingolimod (Gilenya), teriflunomide (Aubagio), BG12, Tecfidera, and alemtuzumab (Campath, Lemtrada).

Cancer is a group of diseases involving abnormal cell growth with the potential to invade or spread to other parts of the body. Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Epcndymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood'; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

The term "chemotherapeutic agent" as used herein refers to any therapeutic agent used to treat cancer. Examples of chemotherapeutic agents include, but are not limited to, Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (dacliximab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, and natalizumab.

A fusion protein of the invention may be used in combination with an immune modulator or chemotherapeutic agent, for example. Treatment with a fusion protein of the invention includes prior to, following or substantially at the same time as other treatments, such as immune modulators or chemotherapeutic agents, for example.

The immune system is a system of biological structures and processes within an organism that protects against disease. This system is a diffuse, complex network of interacting cells, cell products, and cell-forming tissues that protects the body from pathogens and other foreign substances, destroys infected and malignant cells, and removes cellular debris: the system includes the thymus, spleen, lymph nodes and lymph tissue, stem cells, white blood cells, antibodies, and lymphokines. B cells or B lymphocytes are a type of lymphocyte in the humoral immunity of the adaptive immune system and are important for immune surveillance. T cells or T lymphocytes are a type of lymphocyte that plays a central role in cell-mediated immunity. There are two major subtypes of T cells: the killer T cell and the helper T cell. In addition there are suppressor T cells which have a role in modulating immune response. Killer T cells only recognize antigens coupled to Class I MHC molecules, while helper T cells only recognize antigens coupled to Class II MHC molecules. These two mechanisms of antigen presentation reflect the different roles of the two types of T cell. A third minor subtype are the γδ T cells that recognize intact antigens that are not bound to MHC receptors. In contrast, the B cell antigen-specific receptor is an antibody molecule on the B cell surface, and recognizes whole pathogens without any need for antigen processing. Each lineage of B cell expresses a different antibody, so the complete set of B cell antigen receptors represent all the antibodies that the body can manufacture B and T cell attenuator (BTLA or CD272) is an integral part of the immune system. BTLA expression is induced during activation of T cells, and BTLA remains expressed on Th1 cells but not Th2 cells. Like programmed cell death 1 (PD1) and cytotoxic T-lymphocyte associate protein 4 (CTLA4), BTLA activates inhibitory pathways, regulating T cell activation. However, unlike PD-1 and CTLA-4, BTLA displays T-cell inhibition via interaction with tumor necrosis family receptors (TNF-R), not the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses.

The tumor necrosis factor receptor superfamily member (TNFRSF) herpesvirus entry mediator (HVEM) (TNFRSFI4) binds the canonical TNF-related ligands, lymphotoxin-α (LT-α) and LIGHT; however, the distinguishing feature of HVEM is engagement of members of the immunoglobulin superfamily, B and T lymphocyte attenuator (BTLA) and CD160. The ability of HVEM to interact with multiple ligands in distinct configurations creates a functionally diverse set of intrinsic and bidirectional signaling pathways. The capacity to bind these different ligands resides in two different topographical regions in the extracellular domain of HVEM. These distinct sites impart the ability of HVEM to activate both pro-inflammatory and inhibitory pathways. With HVEM at the nexus in several signaling pathways, it is not surprising that it plays important roles in the immune system, such as T-cell costimulation, regulation of dendritic cell (DC) homeostasis, autoimmune-mediated inflammatory responses, as well as host defense against pathogens. HVEM may also play significant roles outside the immune system, in the regulation of sensory neuron development and adipocyte metabolism. The human HVEM protein has 283 amino acids (SEQ ID NO:2). The extracellular domain includes 164 amino acid residues, for example amino acids 39-202. The fusion protein of the present invention includes at least 10, 15, 20, 25, 30, 35, 40, 45, 50, 55, 60, 65, 70, 75, 80, 85, 90, 95, 100, 110, 120, 130, 140, 150, 160, 170 180, 190 or more residues of the HVEM protein (SEQ ID NO:2). The fusion protein of the present invention may include amino acid residues 1-283, 1-202, 1-184, 1-161, 39-202 or 39-161 of the HVEM protein (SEQ ID NO:2), for example.

As used herein the term "non-naturally occurring HVEM protein" refers to an HVEM protein (SEQ ID NO:2, FIG. 19B) containing at least one or more mutations. The fusion protein of the present invention includes at least one mutation, for example S58R, S58K, S58Q, G68T, L70D, L70E, L70N, L70W, L90A or a combination thereof. The fusion protein of the present invention includes at least one additional mutation in the HVEM protein, for example, S58R, S58K, S58Q, G68T, L70D, L70E, L70N, L70W, L90A or a combination thereof. The fusion protein of the present invention may include at least two, three, four or more mutations in the HVEM protein, for example, S58R, S58K, S58Q, G68T, L70D, L70E, L70N, L70W, L90A or a combination thereof. The fusion protein of the present invention includes at least one mutation in the HVEM protein, such as S58R; S58K; S58Q; G68T; L70D; L70E; L70N; L70W; L90A; S58R and L90A; S58R, L70D and L90A; S58R, G68T and L90A; S58R, L70W and L90A; S58R, G68T, L70D and L90A; or S58R, G68T, L70W and L90A.

BTLA uses a distinct surface to interact with HVEM. BTLA/HVEM pathway plays an important role in the maintenance of immune tolerance and the prevention of autoimmune diseases. BTLA-deficient mice develop rheumatoid arthritis, lymphocytic infiltration, autoimmune hepatitis (AIH)-like diseases, and EAE. HVEM-deficient mice show increased susceptibility to MOG peptide-induced EAE and increased T cell proliferation and cytokine production. Antagonistic HVEM-Ig aggravates autoimmunity in collagen-induced arthritis on DBA1 background mice. Thus, the forced expression of BTLA in activated T cells would be a promising strategy for the treatment of autoimmune diseases.

Regarding tumor immunity, tumor antigen-specific $CD8^+$ T cells appear to persistently express BTLA. It has been reported that CpG vaccination partially down-regulates the expression of BTLA in tumor antigen-specific $CD8^+$ T cells and blocks the BTLA/HVEM-mediated inhibitory signal. Although blocking the BTLA/HVEM pathway seems to be relevant as a means to enhance effector T cell functions, careful attention should be paid to the complexity of HVEM-interacting molecules. CD160, an IgSF inhibitory receptor, also binds HVEM. In addition, LIGHT, a TNF family member, delivers a costimulatory signal upon engagement with HVEM. These multiple pathways make it difficult for us to establish novel therapeutic interventions for malignancies.

The manipulation of BTLA/HVEM pathway may become a promising strategy to treat patients with infections. BTLA is induced during *P. berghei* ANKA infection in mice and anti-BTLA antagonistic mAb significantly reduces the incidence of cerebral malaria caused by the protozoa. Thus, pathogens perturbing the BTLA/HVEM pathway may represent ideal targets for anti-BTLA mAb immunotherapy.

Successful activation of inhibitory receptor signaling is dependent on the capacity for receptor agonists to engage configurations of the inhibitor receptor in an activated state, similar to the activated receptor-ligand configuration. A receptor agonist in the form of an antibody will engage particular epitopes of inhibitory receptors such as B and T lymphocyte attenuator (BTLA) that can promote this activated configuration leading to enhanced BTLA signaling. The epitope of these antibodies will not overlap with the binding site of the BTLA receptor Herpesvirus entry mediator (HVEM). These antibodies will function to enhance signaling by activating phosphorylation of the BTLA cytoplasmic domain, and recruitment and phosphorylation of associated proteins, including SHP1 and 2, other signaling proteins recruited to the cytoplasmic domain of BTLA as a marker of activation. The activation of inhibitory signaling downstream of BTLA is predicted to negatively regulate normal signal transduction pathways downstream of the T cell receptor in T cells, and of the B cell receptor in B cells. Additionally, BTLA inhibitory signaling negatively regulates IL-7 and type I interferon cytokine signaling in innate cells such as γδ T cells and natural killer (NK) cells.

The β-herpesvirus Cytomegalovirus (CMV) devotes much of its genome to evasion of the host immune response, and many of these genes are used as the virus progresses towards the establishment of a latent infection. CMV expresses a mimic of HVEM (ORF UL144) that binds BTLA and inhibits T cell proliferation to a greater extent than HVEM. It was recently shown that UL144 does not bind the HVEM receptor CD160, avoiding NK cell activation. Activation of cytolytic cells is also critical in immune responses to cancers, and tumors with mutations in immune recognition pathways are associated with more aggressive tumor outgrowth and mortality. In human follicular lymphoma (FL) the most common secondary mutation occurs in TNFRSF14, while in diffuse large B cell lymphoma (DLBCL) TNFRSF14 is also frequently mutated resulting in gene deletion or loss of expression. However, in a subset of lymphoma several mutations were predicted to impact HVEM ligand binding. It remains unclear how these mutations, or altered ligand interactions may influence lymphoma fitness within the tumor microenvironment.

Similar to the viral UL144 protein, several lymphoma HVEM mutants exhibit ligand selection for BTLA, without binding CD160. The expression of CD160 impedes engagement of wild-type HVEM with BTLA and inhibition of T cell receptor signaling. In contrast, BTLA activation triggered by viral and mutant HVEM is unhindered by CD160 expression. Finally, it was found that activating BTLA inhibits cytokine induced signal transducer and activator of transcription (STAT) phosphorylation in CD160-expressing NK cells, and that the viral UL144 protein more potently inhibits cytokine signaling than wild-type HVEM. Thus, ligand competition hinders HVEM from uniformly engaging inhibitory signals, while ligand selectivity enables viral and mutant HVEM to drive uniquely inhibitory function, indicating a pathway towards development of a BTLA-selective agonist. Together, these data indicate a potential selective pressure for the evolution of UL144 in CMV and for the acquisition of somatic TNFRSF14 mutations in lymphoma, promoting inhibitory and limiting inflammatory signaling in infection and cancer.

In one embodiment, the present invention provides a fusion protein including a non-naturally occurring HVEM protein and an Fc protein, wherein the fusion protein includes an extracellular domain of the HVEM protein and an Fc protein. In one aspect, the fusion protein is a BTLA agonist. In another aspect, the fusion protein includes at least one mutation in the HVEM protein. In an additional aspect, the mutation is S58R, S58K, S58Q, G68T, L70D, L70E, L70N, L70W, L90A or a combination thereof. In one aspect, the fusion protein further includes at least one mutation in the HVEM protein, for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A. In one aspect, the Fc protein is IgA, IgG, IgD, IgE or IgM. In another aspect, the Fc protein is IgG1, IgG2, IgG3 or IgG4. In a specific aspect, the IgG Fc protein is human.

In an additional embodiment, the present invention provides a pharmaceutical composition including a fusion protein such as a non-naturally occurring HVEM protein and an Fc protein and a pharmaceutically acceptable carrier. In one aspect, the fusion protein is a BTLA agonist. In another aspect, the fusion protein includes an extracellular domain of the HVEM protein and an Fc protein. In another aspect, the fusion protein includes at least one mutation in the HVEM protein. In an additional aspect, the mutation is S58R, S58K, S58Q, G68T, L70D, L70E, L70N, L70W, L90A or a combination thereof. In an additional aspect, the fusion protein further includes at least one mutation in the HVEM protein for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A. In one aspect, the Fc protein is IgA, IgG, IgD, IgE or IgM. In another aspect, the Fc protein is IgG1, IgG2, IgG3 or IgG4. In a specific aspect, the IgG Fc protein is human.

In one embodiment, the present invention provides a method of treating a BTLA related disorder including administering a fusion protein such as a non-naturally occurring HVEM protein and an Fc protein to a subject in need thereof, thereby treating the BTLA related disorder. In one aspect, the BTLA related disorder is cancer or an autoimmune disease or disorder. In an additional aspect, the autoimmune disease or disorder is Addison's disease; amyotrophic lateral sclerosis, Crohn's disease, Cushing's Syndrome, diabetes mellitus type 1, graft versus host disease, Graves' disease, Guillain-Barré syndrome, lupus erythematosus, multiple sclerosis, psoriasis, psoriatic arthritis, rheumatoid arthritis, sarcoidosis, scleroderma, systemic lupus erythematosus, transplant rejection, or vasculitis. In another aspect, the cancer is prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract. In a further aspect, BTLA signaling is increased. In another aspect, the fusion protein is a BTLA agonist.

In one aspect, the fusion protein includes an extracellular domain of the HVEM protein and an Fc protein. In an additional aspect, the fusion protein includes amino acid residues 39-161 of SEQ ID NO:2 and an Fc protein. In a further aspect, the Fc protein is IgA, IgG, IgD, IgE or IgM. In certain aspects, the Fc protein is IgG1, IgG2, IgG3 or IgG4. In a specific aspect, the IgG Fc protein is human. In one aspect, the fusion protein includes at least one mutation in the HVEM protein. In an additional aspect, the mutation is S58R, S58K, S58Q, G68T, L70D, L70E, L70N, L70W, L90A or a combination thereof. In one aspect, the fusion protein further includes at least one mutation in the HVEM protein, for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A.

In one aspect, the method also includes administering an immune response modulator or chemotherapeutic agent. In another aspect, the immune response modulator is eicosanoids, cytokines, prostaglandins, interleukins, chemokines, check point regulators, TNF superfamily members, TNF receptor superfamily members and/or interferons. In an additional aspect, the immune response modulator is CXCL-8, CCL2, CCL3, CCL4, CCL5, CCL11, CXCL10, IL1 IL2, IL3, IL4, IL5, IL6, IL7, IL8, IL9, IL10, IL11, 1L12, IL13, IL15, IL17, IL17, IFN-α, IFN-β, IFN-ε, IFN-γ, G-CSF, TNF-α, CTLA4, CD20, PD1, PD1L1, PD1L2, ICOS, CD200, CD52, LTα, LTαε, LIGHT, CD27L, 41BBL, FasL, Ox40L, April, TL1A, CD30L, TRAIL, RANKL, BAFF, TWEAK, CD40L, EDA1, EDA2, APP, NGF, TNFR1, TNFR2, LTβR, HVEM, CD27, 4-1BB, Fas, Ox40, AITR, DR3, CD30, TRAIL-R1, TRAIL-R2, TRAIL-R3, TRAIL-R4, RANK, BAFFR, TACI, BCMA, Fn14, CD40, EDAR XEDAR, DR6, DcR3, NGFR-p75, and/or Taj. In a certain aspects, the immune response modulator is tocilizumab (Actemra), CDP870 (Cimzia), enteracept (Enbrel), adalimumab (Humira), Kineret, abatacept (Orencia), infliximab (Remicade), rituximab (Rituxan), golimumab (Simponi), Avonex, Rebif, ReciGen, Plegridy, Betaseron, Copaxone, Novatrone, natalizumab (Tysabri), fingolimod (Gilenya), teriflunomide (Aubagio), BG12, Tecfidera, and/or alemtuzumab (Campath, Lemtrada).

In a further aspect, the chemotherapeutic agent is Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (dacliximab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, and/or natalizumab. In one aspect, phosphorylation of ERK1/2 and/or ZAP70/Syk is reduced. In another aspect, total cellular phosphorylation and phosphorylation of SHP2 is induced.

In a further embodiment, the present invention provides a method of modulating an immune response in a subject including administering a fusion protein such as a non-naturally occurring HVEM protein and an Fc protein to the subject, thereby modulating the immune response. In one aspect, the fusion protein is a BTLA agonist. In another aspect, the fusion protein includes the extracellular domain of the HVEM protein and an Fc protein. In another aspect, the fusion protein includes at least one mutation in the HVEM protein. In an additional aspect, the mutation is S58R, S58K, S58Q, G68T, L70D, L70E, L70N, L70W, L90A or a combination thereof. In an additional aspect, the fusion protein further includes at least one mutation in the HVEM protein, for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A. In one aspect, the Fc protein is IgA, IgG, IgD, IgE or IgM. In another aspect, the Fc protein is IgG1, IgG2, IgG3 or IgG4. In a specific aspect, the IgG Fc protein is human. In one aspect, BTLA signaling is increased. In another aspect, phosphorylation of ERK1/2 and/or ZAP70/Syk is reduced. In an additional aspect, total cellular phosphorylation and phosphorylation of SHP2 is induced. In a further aspect, the subject has a BTLA related disease or disorder. In certain aspects, the BTLA related disease is cancer or an autoimmune disease or disorder.

In one embodiment, the present invention provides a method of modulating BTLA signaling in a cell, including contacting a BTLA expressing cell with a fusion protein such as a non-naturally occurring HVEM protein and an Fc protein, thereby modulating BTLA signaling. In one the BTLA signaling is increased. In another aspect, the fusion protein includes an extracellular domain of the HVEM protein and an Fc protein. In another aspect, the fusion protein includes at least one mutation in the HVEM protein.

In an additional aspect, the mutation is S58R, S58K, S58Q, G68T, L70D, L70E, L70N, L70W, L90A or a combination thereof. In an additional aspect, the fusion protein further includes at least one mutation in the HVEM protein, for example, S58R, S58K, S58Q, G68T, L70D, L70E, L70N, L70W, L90A or a combination thereof. In another aspect, the fusion protein includes at least two, three, four or more mutations in the HVEM protein, for example, S58R, S58K, S58Q, G68T, L70D, L70E, L70N, L70W, L90A or a combination thereof. In certain aspects, the fusion protein includes at least one mutation in the HVEM protein, such as S58R; S58K; S58Q; L70D; L70E; L70N; L90A; S58R and L90A; S58R and G68T; S58R and L70W; S58R, L70D and L90A; S58R, G68T and L90A; S58R, L70W and L90A; S58R, G68T, L70D and L90A; or S58R, G68T, L70W and L90A. In one aspect, the Fc protein is IgA, IgG, IgD, IgE or IgM. In another aspect, the Fc protein is IgG1, IgG2, IgG3 or IgG4. In a specific aspect, the IgG Fc protein is human. In one aspect, phosphorylation of ERK1/2 and/or ZAP70/Syk is reduced. In another aspect, total cellular phosphorylation and phosphorylation of SHP2 is induced.

The invention in all its aspects is illustrated further in the following Examples. The Examples do not, however, limit the scope of the invention, which is defined by the appended claims.

EXAMPLES

Example 1

UL144 Residues Homologous to HVEM are Required for Binding to BTLA

Figures 7A, 7B, 7C, 7D, 7E:
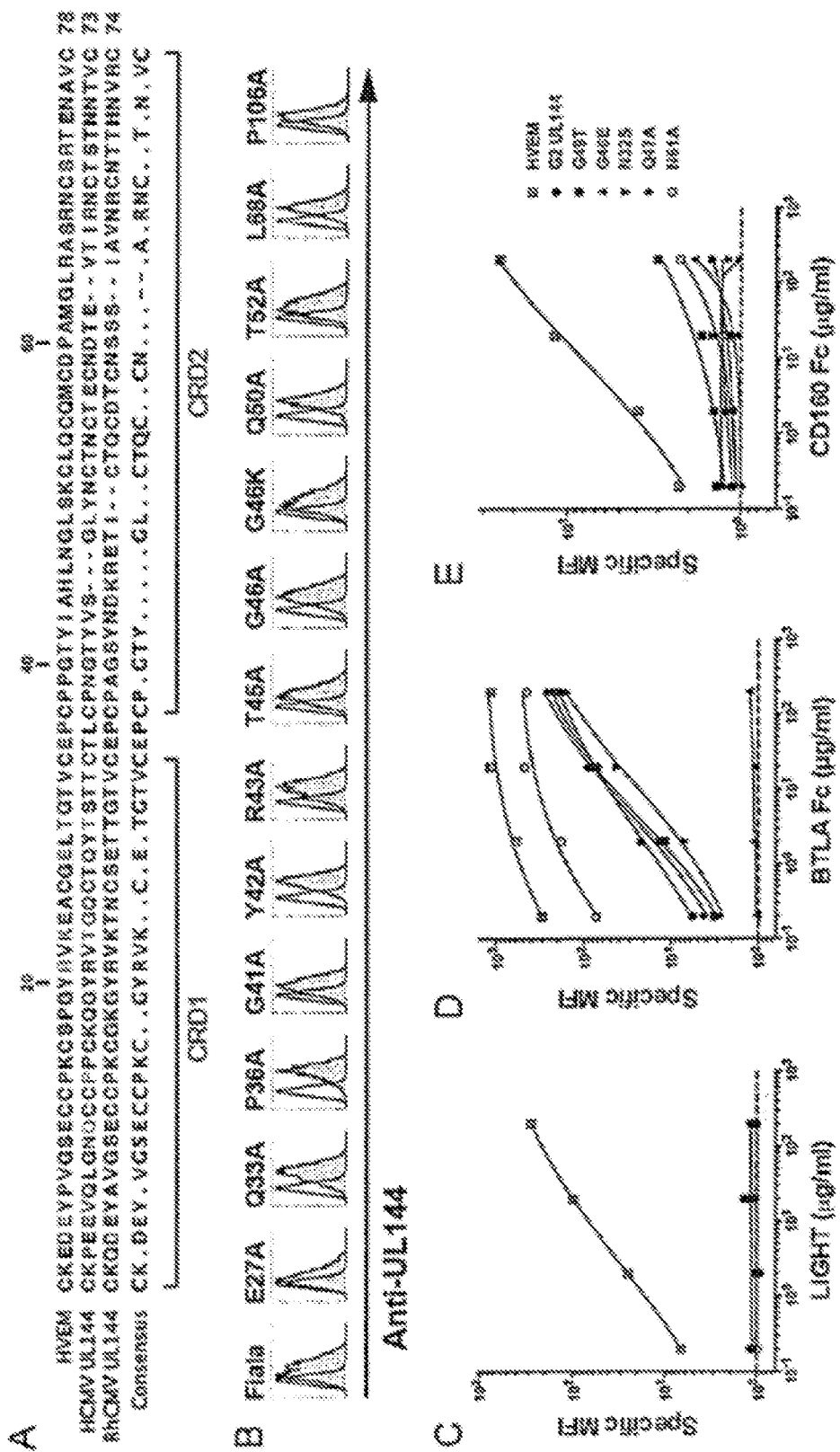
FIGS. 7A-E show mutations that effect UL144 binding to BTLA.

Human CMV encoded UL144 selectively binds BTLA but not CD160 and inhibits T cell proliferation activated by T cell receptor signaling to a greater extent than HVEM proteins. To determine whether the selection for BTLA by UL144 resulted from unique interactions between the surfaces of these two proteins the structure of the BTLA contact surface of UL144 was modeled on the previously solved HVEM-BTLA co-crystal (FIG. 1A). Next, the UL144 surface residues that were divergent from HVEM by alanine- and homology-scanning mutagenesis to screen potential BTLA binding surfaces were targeted (FIG. 1). It was observed mutation in several UL144 residues disrupted or reduced binding of BTLA that define a surface centered on one face of the CRD1 region similar to the BTLA binding surface of HVEM. The most critical mutations validated to be surface expressed occur at Gly41 and Tyr42, homologous to Gly60 and Tyr61 in HVEM (FIG. 7). None of the homology-scanning mutations in UL144 revealed additional ligand binding to CD160 or to the TNFSF ligand, LIGHT, although the G46K and N61A mutants enhanced binding to BTLA (FIG. 1B, C and FIG. 7). Thus, no single mutation restores CD160 binding to the UL144 protein, indicating that CMV likely has evolved UL144 to select for BTLA binding through multiple genetic modifications. Specific residues impact BTLA binding: $Glu^{27}$, $Gln^{33}$, $Pro^{36}$, $Gly^{41}$, $Tyr^{42}$, $Thr^{52}$, $Leu^{68}$ appear to be required; $Arg^{43}$, $Thr^{45}$ have reduced binding; $Asn^{32}$, $Gln^{47}$, $Gly^{49}$, $Gln^{50}$ appear to have no effect; $Gly^{46}$, $Asn^{61}$ increase binding.

Cells and surface protein expression: EL4 and 293T cells were maintained in DMEM with 10% heat-inactivated FBS, antibiotics, L-glutamine and 50 µM 2-ME. NK92 cells were maintained in RPMI with 8% heat-inactivated FBS, 8% equine serum, antibiotics, L-glutamine and 50 µM 2-ME supplemented with 100 U/ml IL-2. BJAB and Jurkat TAg (JTAg) cells were maintained in RPMI with 10% heat-inactivated FBS, antibiotics, L-glutamine, and 50 µM 2-ME. EL4 cells and BJAB cells transduced with retroviruses containing wild-type and mutant human BTLA (Watanabe et al. (2003); Nat Immunol 4:670) were sorted for GFP expression to increase the frequency of BTLA expressing cells. Pseudotyped single infection retrovirus was produced by co-transfection of retroviral plasmid, pCG VSVg envelope protein, and Hit60 gag-pol as previously described (Sedy et al. (2005), Nat Immunol 6:90). UL144 and BTLA mutants were produced by round-the-world PCR mutagenesis. 293T cells transduced by calcium phosphate transfection with pND vector containing mutant or wild-type UL144 were used for Fc binding studies. All oligonucleotides used for PCR amplification and site-directed mutagenesis are listed in Table 1. For transient expression of HVEM ligands in JTAgs, cells were electroporated with 10 µg of the indicated DNA constructs with control vector at 230V for 65 ms using a T820 square wave electroporator.

Antibodies and Fc fusion proteins: Anti-human HVEM was from BD Biosciences. Anti-human BTLA antibodies clones MIH26 and J168 were obtained from eBioscience and BD Biosciences. Anti-human BTLA clone 6F4 and anti-UL144 clone 2F11 were produced as previously described (Cheung et al. (2005), Proc Natl Acad Sci 102: 11318; Cheung et al. (2009a), J Immunol 183:7286). Donkey anti-human Fcγ and anti-Fcµ F(ab')$_2$ were from Jackson Immunoresearch. Antibodies to identify human PBMC populations include CD19 FITC, CD56 PE-Cy7, CD8 PE, CD3 PE 610, CD4 eFluor450, and CD69 PerCP-Cy5.5. Phospho-specific antibodies include phospho-tyrosine PE, phospho-Akt (S473) PE, and phospho-SHP-2 (Y542) Alexa647, phospho-ERK1/2 (pT202/pY204) PerCP-e710, and phospho-NF-κB p65 (S529) PE. The Fc fusion proteins were designed and produced as follows: The ectodomain (residues 1-184) including the native signal sequence of human HVEM was fused at the 3' end to the human IgG Fc sequence. For human BTLA and CMV UL144, residues 26-150 and 19-132, respectively, were fused at the 5' end to the human Ig signal sequence and the 3' end to the human IgG Fc regions. The Fc fusion proteins were produced in transfected 293T cells grown in CeliGro Free serum free medium and purified by affinity chromatography on protein A columns. Control human IgG1 protein was from Sigma-Aldrich. BTLA selective HVEM mutant proteins were engineered de novo through three rounds of mutagenesis as follows: first, alanine mutagenesis of surface exposed residues to identify ligand-binding hotspots; second, saturation mutagenesis at hotspots to optimize targeting of ligand binding; third, combinatorial mutagenesis to achieve BTLA selectivity and enhance affinity.

Binding Assays: Flow cytometric binding assays were performed as previously described (Sedy et al., 2013). Briefly, cells were incubated with Fc ligands for 30 min on ice in buffer (PBS with 2% FBS), washed twice, incubated with anti-Fc secondary for 15 min on ice in buffer, washed twice, and analyzed. Specific mean fluorescence intensity (MFI) was calculated by subtracting experimental cellular MFI from control cellular MFI.

Surface Plasmon Resonance kinetic affinity measurement: Human BTLA-Fc ligand was immobilized onto a CM5 sensor chip to 150 Response Units using amine coupling. Sensograms were collected at a flow rate of 30 µl/min, 25° C. Specific binding was determined by subtraction of control from ligand channels. Indicated concentrations of analyte were injected from vials cooled to 7° C. Data collection includes 3 minutes of 90 µl analyte followed by 15 minutes disassociation. Regeneration after each cycle was with a 30 second pulse of 15 µl 10 mM Glycine pH 2.5. The first 10 seconds following analyte injection and disassociation were applied for affinity measurements with both the Langmuir and the Bivalent fit models of BIAevaluation software (version 4.1) kinetic analysis module.

Phosphoflow analysis of microsphere activated cells: Aldehyde/sulfate latex microspheres (5 µm) were covalently coupled to 100 µg/ml of anti-Fcµ F(ab')$_2$ alone or with the indicated concentrations of human IgG1, HVEM-Fc, or UL144-Fc as previously described (Sperling et al. (1998), J immunol 161:6459). Briefly, microspheres were washed in PBS, incubated with the indicated proteins at 37° C. for 90 min, blocked in buffer (PBS with 1% BSA and 0.1% glycine), washed twice, resuspended in media, and counted. Microspheres were used to stimulate JTAg and BJAB cells at a 3:1 ratio. Microspheres were added first to 96 well flat bottom plates followed by cells washed in PBS and resuspended to a concentration of 1.5×10$^6$ cells/ml. Plates were briefly spun and incubated for the indicated times at 37° C. followed by fixation with 2% paraformaldehyde in PBS and additional incubation at 37° C. for 10 min. Cells were washed in buffer (PBS with 2% FBS) and permeabilized in Perm III Buffer (BD Bioscience) for 30 min on ice, washed twice, incubated with phospho-specific antibodies for 30 min on ice, washed twice and analyzed.

Western Blotting: The IL-2-dependent NK92 model cell line was activated using the indicated concentrations of IL-2 or Interferon-β. In experiments testing IL-2 responses, NK92 cells were cultured overnight without IL-2 to re-establish basal signaling. In experiments using fusion proteins and antibodies, NK92 cells were coated with control human IgGI, HVEM-Fc, or UL144-Fc or control mouse IgG2a or anti-BTLA for at least 15 minutes on ice prior to activation. NK92 cells were aliquoted to 2×10$^6$ cells per condition in 100 µl and activated at 37° C. for the indicated times, quenched with ice cold PBS and lysed in RIPA buffer at 4° C. for 20 minutes followed by centrifugation at 14,000 rpm, 4° C. Extracts were boiled in SDS loading buffer containing 1% β-mercaptoethanol for 5 minutes and resolved by SDS-PAGE on 10% Bis-Tris gels. Proteins were transferred using tank method to PVDF membrane and blocked with 1% ovalbumin in TBS-T buffer, and blotted with antibodies against phospho-JAK1, phospho-STAT5, phospho-STAT1, phospho-Akt (S473), and total actin, followed by anti-rabbit HRP or anti-mouse HRP and visualized by enhanced chemiluminescence.

Cytokine activation of Human PBMC: Fresh human blood was collected and prepared from healthy donors as previously described (Sedy et al., 2013). Briefly, PBMC isolated from Ficoll gradient buffy coats were incubated at 106 cells/ml with indicated Fc proteins on ice for 15 min, followed by crosslinking with 5 µg/ml of anti-human Fcγ F(ab')2 for 6 hours prior to flow cytometric analysis.

Example 2

Somatic TNFRSF14 Mutations in Lymphoma Target Ligand Binding

Figures 2A, 2B, 2C, 2D, 2E, 2F, 2G, 2H:
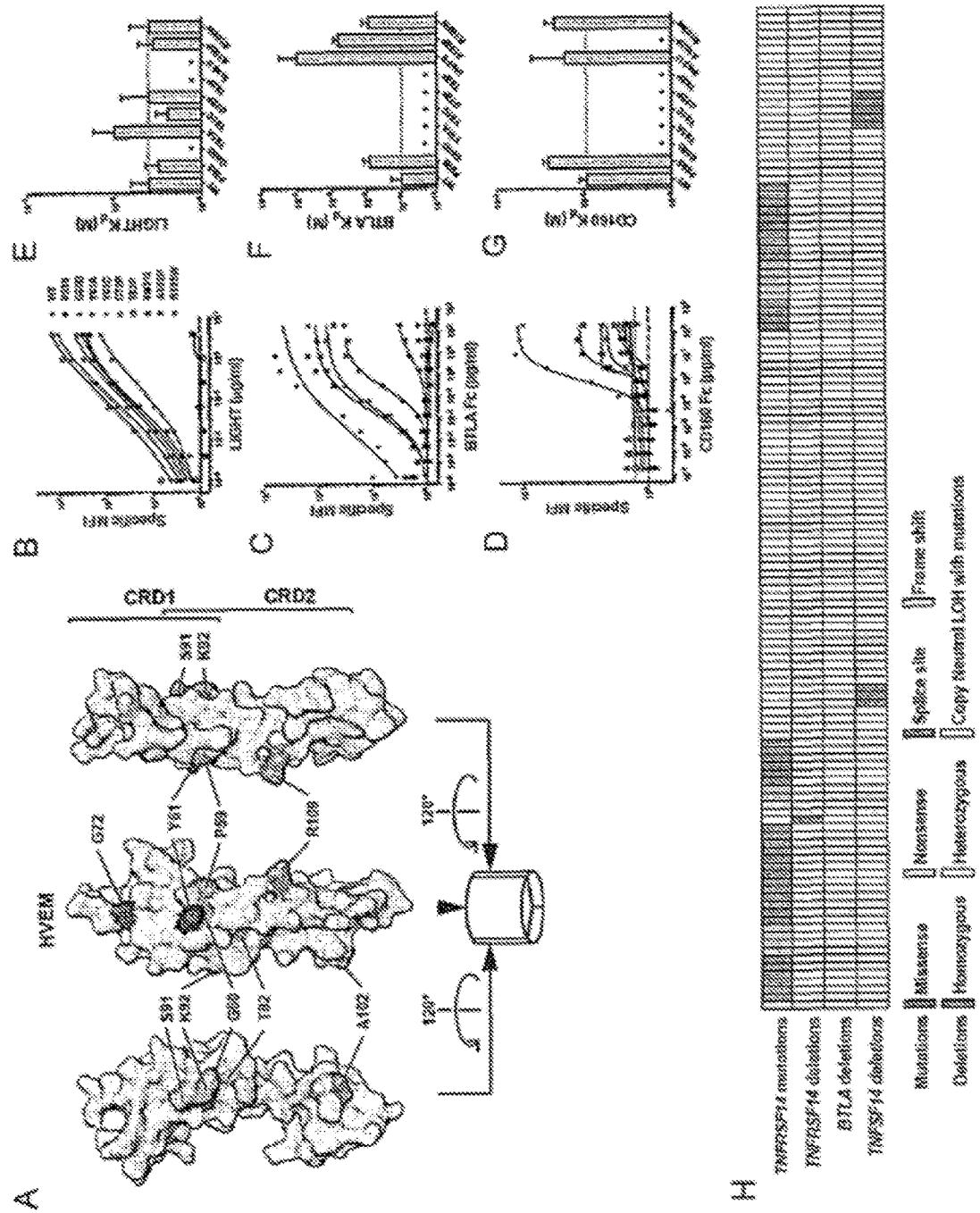
FIGS. 2A-H show the identification of HVEM-ligand binding mutants in human lymphoma.
Figures 8A, 8B:
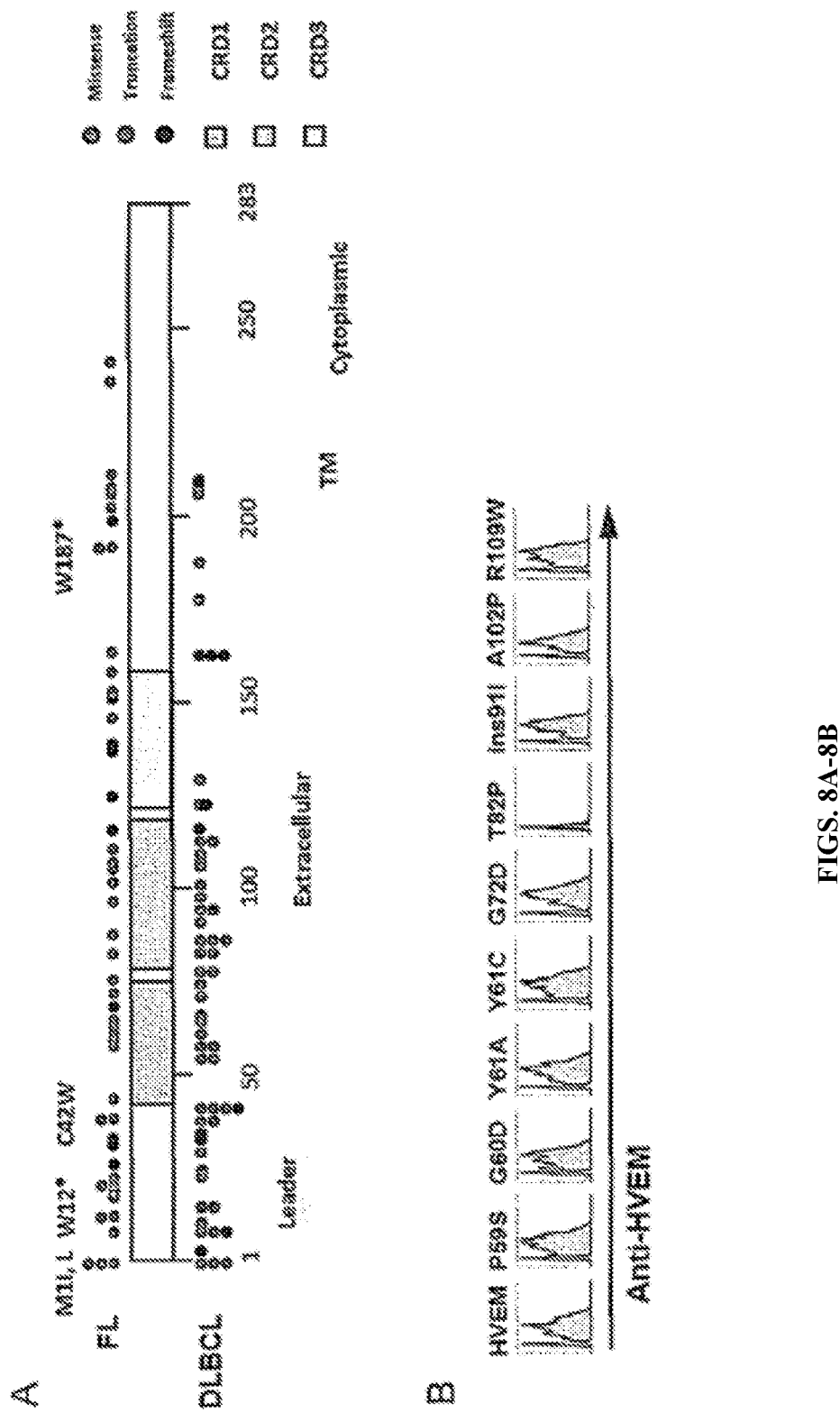
FIGS. 8A-B show the identification of HVEM-ligand binding mutants in human lymphoma.

It was noted that somatic TNFRSF14 mutations acquired in FL and DLBCL have the potential to interrupt conserved HVEM interactions with its ligands, and subsequent function (FIG. 8). Lymphoma-associated mutations were selected that were not predicted to disrupt the HVEM structure and assessed mutant receptor binding to BTLA, CD160, and LIGHT. HVEM mutants validated to be surface expressed could be categorized into three groups according to their effects on ligand binding (FIG. 8). Mutations containing P59S, A102P, or R109W disrupted interactions with CD160 alone. Y61C and G72D mutations abrogated interactions with both BTLA and CD160, but did not greatly affect LIGHT binding. Finally, mutants G60D and T82P, or an insertion of Ile between Ser91 and Lys92 disrupted all ligand interactions (FIG. 2). HVEM Tyr61 has been identified as critical for binding both BTLA and CD160. Together, these somatic mutations define a hierarchy of ligand binding with preferential loss of interactions with CD160 and BTLA, and either unimpaired or also affected interactions with LIGHT. The genetic alterations in TNFSF14 were further confirmed in an additional cohort of DLBCL, and identified additional tumors with deletions in BTLA or TNFSF14 (FIG. 2H). The presence of multiple genetic lesions in the HVEM network within human FL and DLBCL indicates that these pathways may significantly contribute to cellular selection within the tumor microenvironment. Specific residues are important for ligand binding: Pro$^{59}$, Ala$^{102}$, Arg$^{109}$-no binding to CD160; Tyr$^{61}$ and Gly$^{72}$ no binding to BTLA or CD160; Gly$^{60}$, Thr$^{82}$, and ins91I (indicated at Ser$^{91}$ and Lys$^{92}$)-no binding to LIGHT, BTLA, or CD160 (FIG. 2C-H).

Example 3

HVEM and UL144 Bind Overlapping Surfaces of BTLA

Figures 3A, 3B, 3C, 3D, 3E:
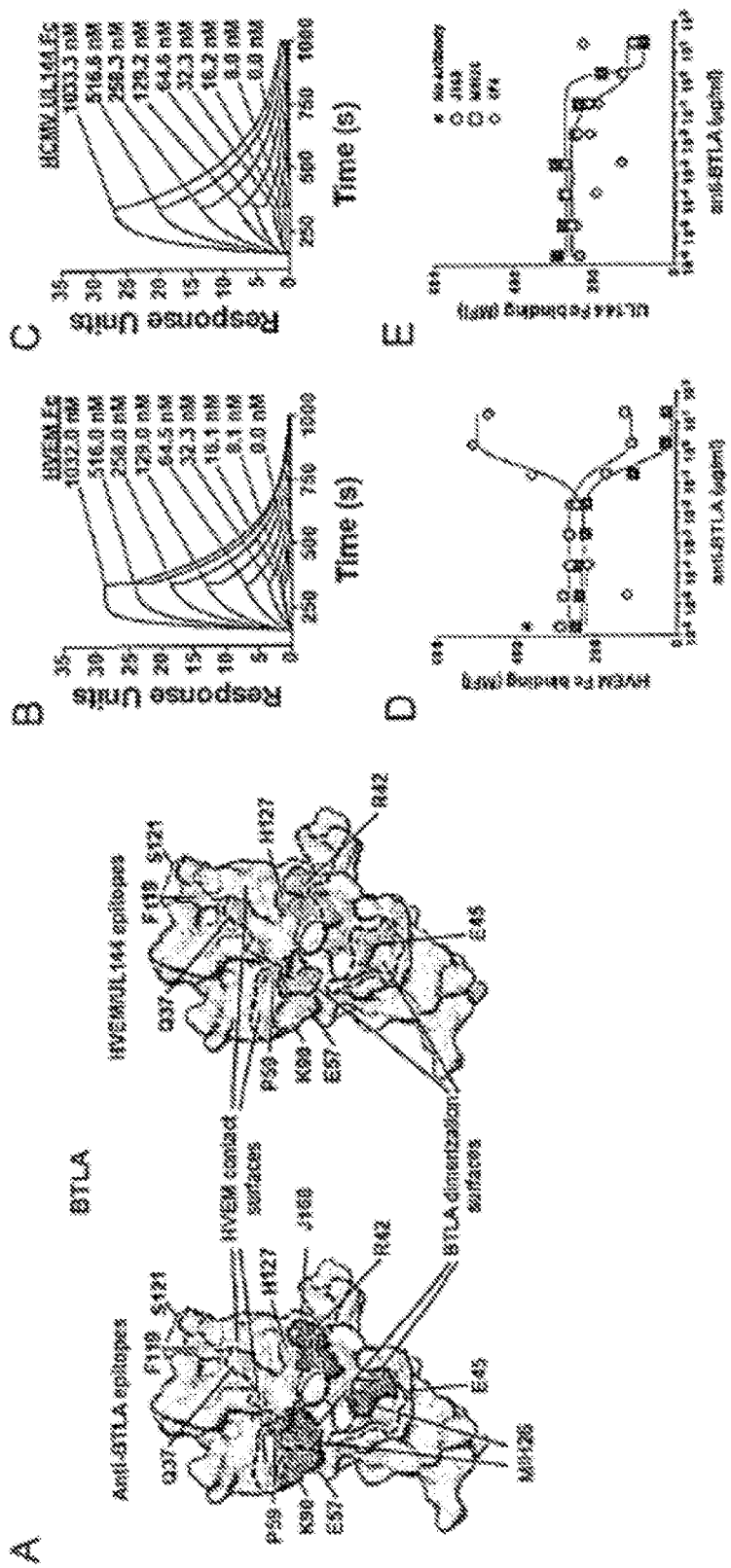
FIGS. 3A-E show that HVEM and UL144 bind the same surface of BTLA.
Figures 9A, 9B, 9C, 9D, 9E, 9F:
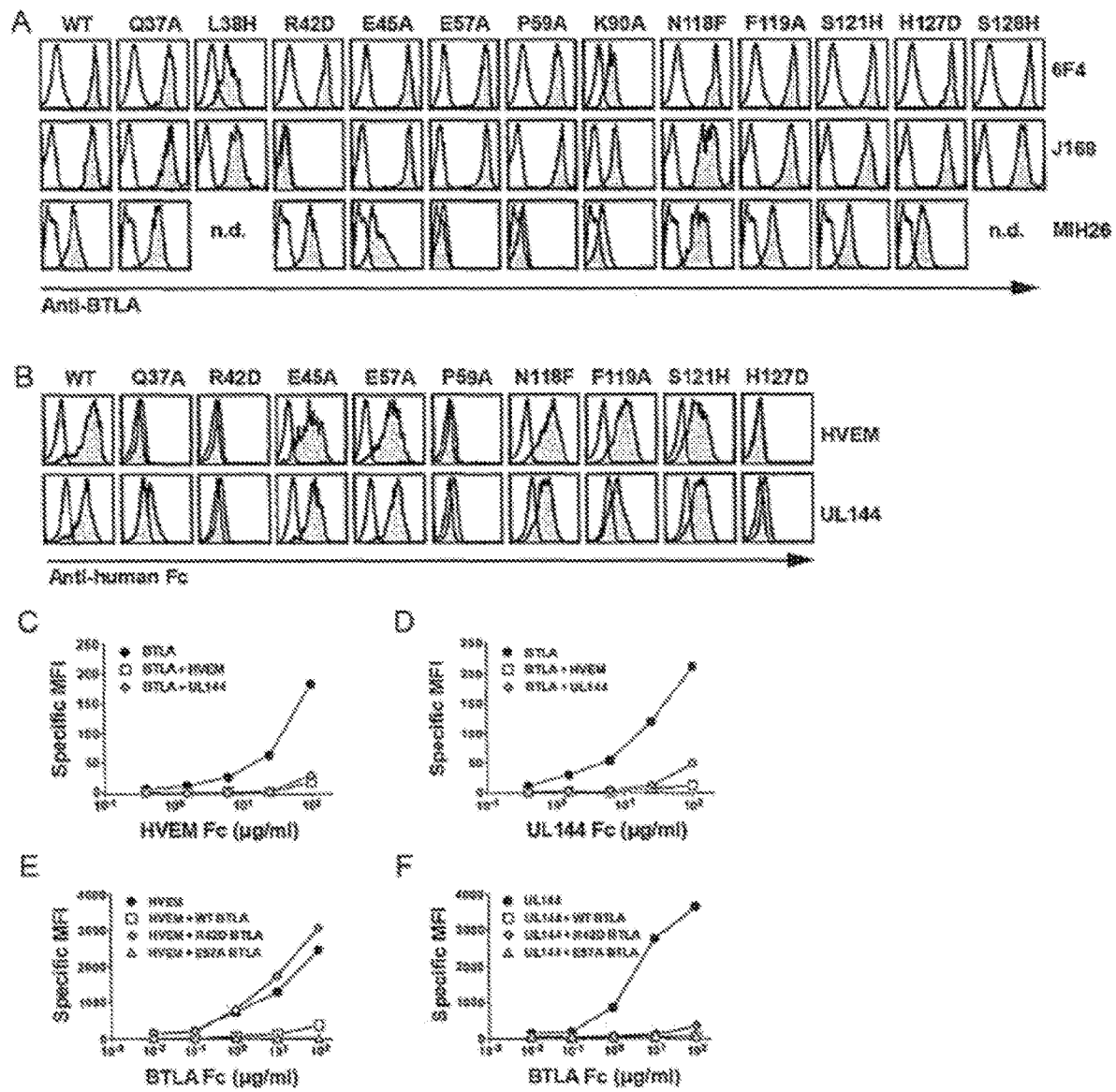
FIGS. 9A-F show that HVEM and UL144 bind the same surface of BTLA.

To determine whether altered BTLA activity by viral UL144 or mutant HVEM was due to engagement of different surfaces, BTLA residues in contact surfaces for these agonists were compared. It was found that binding of the anti-BTLA mAb (clone MIH26) previously shown to have agonistic activity was disrupted by mutation at either Glu57 or Pro59, while binding of the competitive anti-BTLA mAb (clone J168) was disrupted by mutation at Arg42 (FIG. 3A and FIG. 9A). Notably, the M1H26-binding residue Glu57 is homologous to Gln63 in mouse BTLA, which is contained within the epitope of the agonistic anti-BTLA mAb (clone 6A6). In comparison, similar requirements were observed for binding of both HVEM-Fc and UL144-Fc to Gln37, Arg42, Pro59 and His127, consistent with previous studies in human and mouse BTLA. Similar affinities for BTLA to HVEM or UL144 were confirmed using surface plasmon resonance (FIG. 3B, C). The avidity (KD, 1:1 binding model) of UL144-Fc for BTLA (295 nM) was slightly less than HVEM-Fc (177 nM) (Table 2). While subtle avidity and binding differences were observed between HVEM and UL144, overall human CMV UL144 closely mimics HVEM binding to BTLA. FIGS. 9A-B show EL4 cells transduced with wild-type or mutant human BTLA were stained with anti-human BTLA polyclonal or monoclonal antibodies or with of HVEM-Fc or human CMV UL144-Fc, followed by species specific secondary. From top to bottom graphs show specific MFI staining of 6F4, J168, or MIH26 anti-BTLA (A), or HVEM-Fc or UL144-Fc (B) staining on cells gated on GFP expression.

HVEM and BTLA co-expression in lymphocytes leads to the formation of an intrinsic complex in cis located at the cell surface that competitively blocks activation by extrinsic ligands in trans. It was determined whether UL144 co-expressed with BTLA formed complexes in cis to prevent ligand access in trans, or whether UL144 ligation of BTLA in trans might circumvent the steric hindrance of BTLA access by HVEM. Both HVEM and UL144 co-expressed with BTLA blocked binding to both HVEM-Fc and UL144-Fc, indicating that HVEM and UL144 form similar complexes with BTLA in cis, and that UL144 cannot outcompete a preformed BTLA cis complex at cell surfaces (FIG. 9C, D). However, co-expression of the BTLA R42D mutant did prevent cis-expressed HVEM, but not UL144, from binding to BTLA-Fc in trans, indicating that a single mutation may not be sufficient to disrupt the BTLA-UL144 cis-complex (FIG. 9E, F).

The antibody epitopes recognized by mAb J168 and MIH26 overlap with the surface of BTLA occluded by HVEM molecules in the tetrameric asymmetric unit, and were predicted to block HVEM binding to BTLA (FIG. 3A). While titration of both of these anti-BTLA clones interfered with HVEM-Fc and UL144-Fc binding to BTLA, a third anti-BTLA mAb (clone 6F4) enhanced binding of HVEM-Fc to BTLA, but did not affect binding of UL144-Fc (FIG. 3D, E). Its epitope was not identified using these BTLA mutants, and this clone does not show any reactivity to HVEM. Together, these data indicate that while the same surface of BTLA appears to be used to bind HVEM and UL144, there may be additional structural elements that contribute to ligand binding. Additionally, epitope mapping of BTLA antibodies indicates that agonistic activity is linked to Glu57 or Pro59 on human BTLA (for clone MIH26) and Gln63 on mouse BTLA (for clone 6A6). In FIG. 3, the left image specific residues indicate a requirement for antibody binding: Glu45, Glu57, Pro59 are required for MIH26 binding, Arg42 is required for J168 binding. In FIG. 3, the right image specific residues indicate the HVEM/UL144 binding epitope: Gln37, Arg42, Pro59, His127 appear to be required for HVEM/UL144 binding, Glu45, Glu57, Phe119, Ser121 appear to not be required for HVEM/UL144 binding.

Example 4

CD160 Limits BTLA-Mediated Inhibition Through Competition for HVEM

Figures 4A, 4B, 4C:
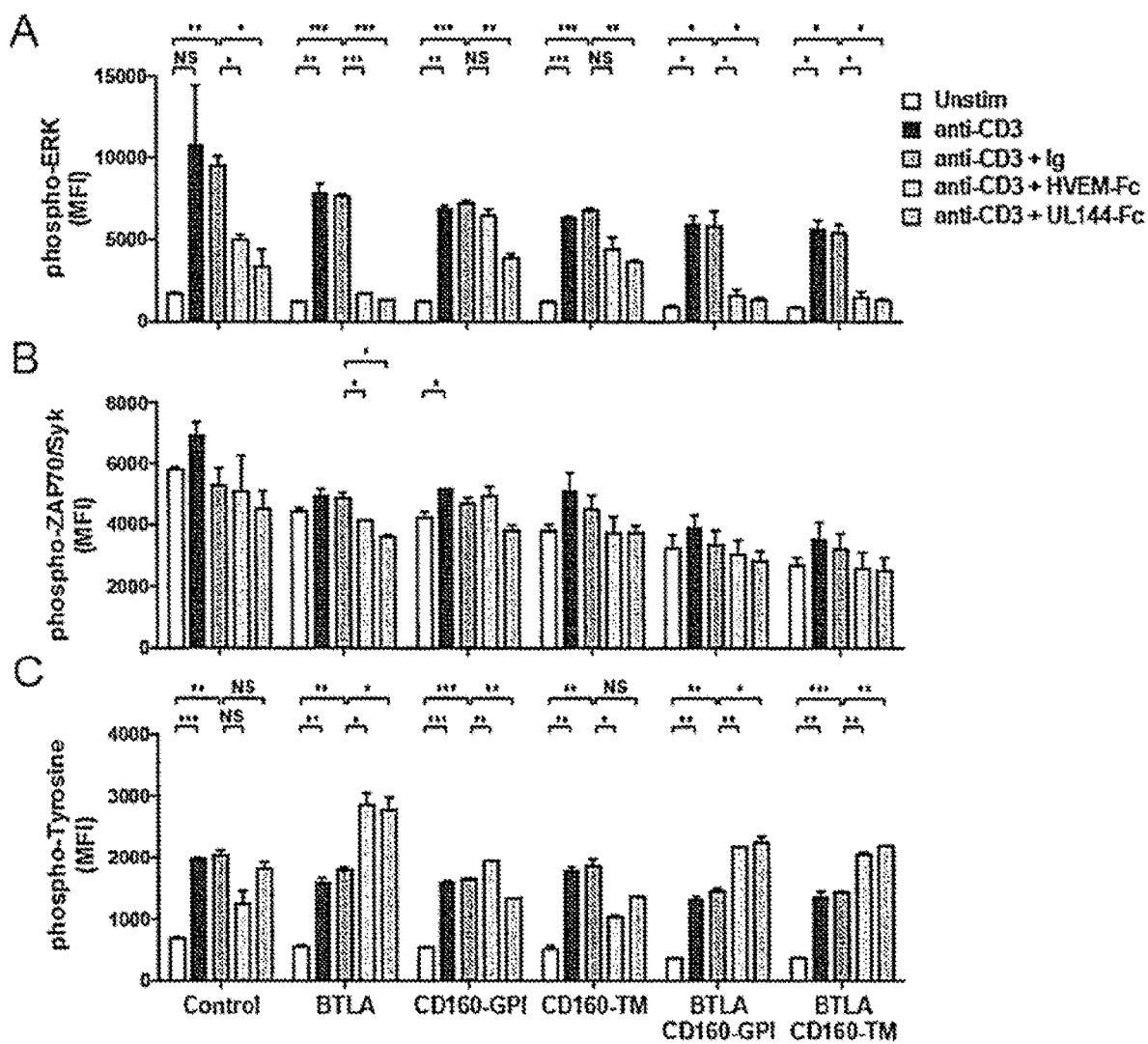
FIGS. 4A-C show that CD160 limits HVEM activation of BTLA.
Figures 10A, 10B:
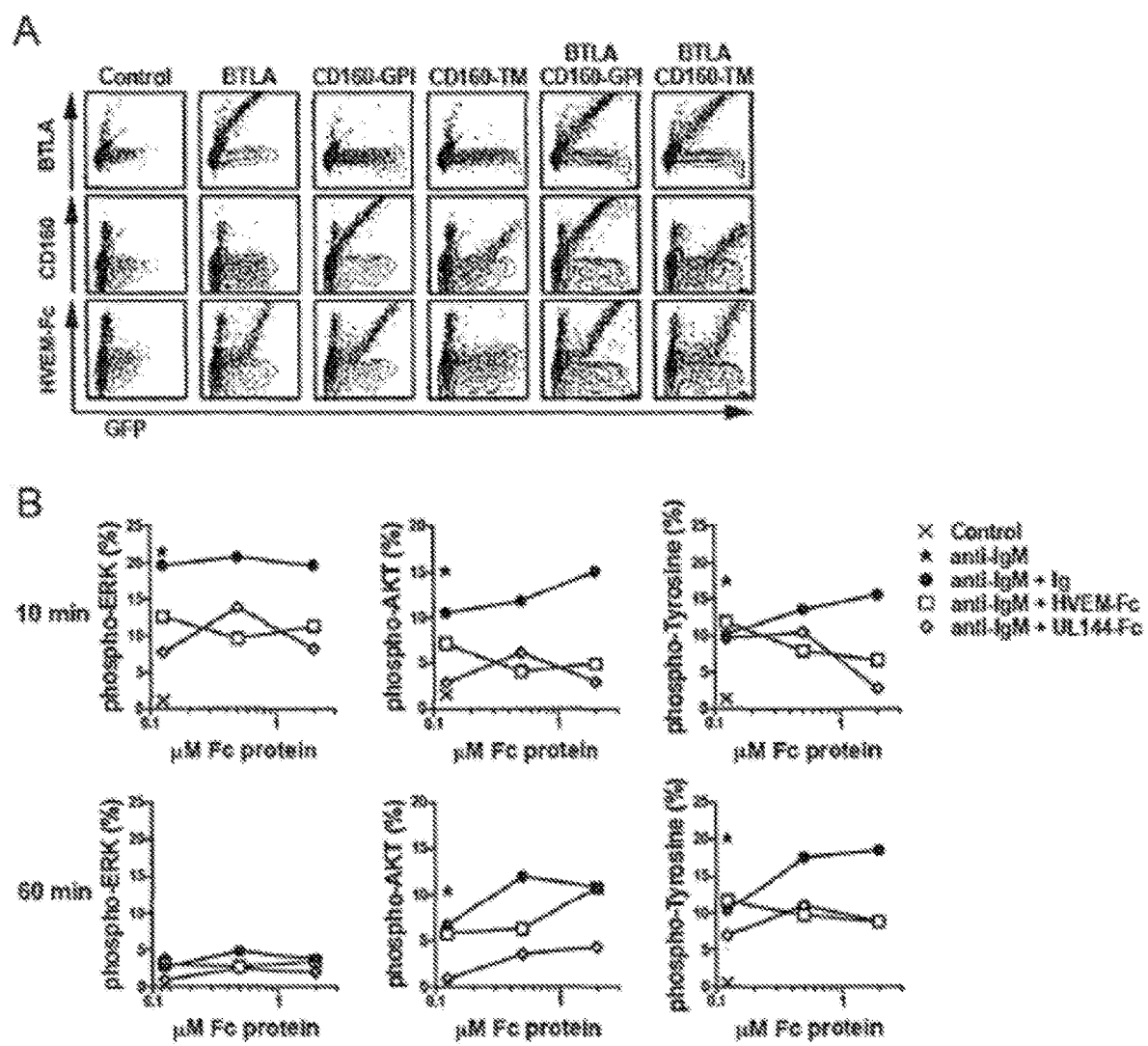
FIGS. 10A-B show that CD160 limits HVEM activation of BTLA.

The expression of CD160 and LIGHT in diverse lymphocyte subsets may influence the capacity of viral and cancer mutant HVEM to engage BTLA inhibitory signaling. To assess whether altering the expression of HVEM ligands influenced BTLA agonism, Jurkat T cells expressing ectopic BTLA or CD160 isoforms were activated (FIG. 4 and FIG. 10A). Control cells activated with immobilized anti-CD3 induced phosphorylation of extracellular signal-regulated kinase (ERK) 1/2, zeta-chain associated protein kinase 70 kD (ZAP70)/Syk, and total cellular tyrosine, while ERK1/2 phosphorylation was reduced in cells activated with co-immobilized anti-CD3 and HVEM or UL144-Fc (~50-70% reduction). Ectopic BTLA expression enhanced the ability of HVEM and UL144 to inhibit ERK1/2 phosphorylation to background levels, correlating with significantly reduced ZAP70/Syk phosphorylation (~15-25%) (FIG. 4A, B). Tyrosine phosphorylation was increased following stimulation with HVEM or UL144, reflecting activation of BTLA and associated signaling proteins (FIG. 4C). Importantly, in cells expressing ectopic CD160 (glycophosphoinositide or transmembrane isoforms), HVEM was unable to inhibit ERK1/2 phosphorylation unless BTLA was additionally present. In contrast, UL144 inhibited ERK1/2 phosphorylation regardless of CD160 isoform expression. The agonistic activity of HVEM and UL144 were confirmed in the human non-Hodgkins lymphoma, BJAB, which expresses high levels of human BTLA in the absence of other HVEM ligands and activates Syk-dependent ERK and Akt phosphorylation in response to IgM stimulation (FIG. 10B). Specifically, in cells activated with co-immobilized anti-IgM and titrated HVEM or UL144-Fc, approximately 50% reductions in phosphorylation of ERK, Akt, and cellular phosphotyrosines was observed compared to control cells. Together, these results illustrate that the capacity for HVEM to activate BTLA signaling is dependent on the relative ratio of BTLA to CD160, and that receptor selectivity by a viral mimic results in unhindered BTLA agonism.

Example 5

Agonist Activation of BTLA Inhibits Pro-Inflammatory Cytokine Stimulation

Figures 5A, 5B:
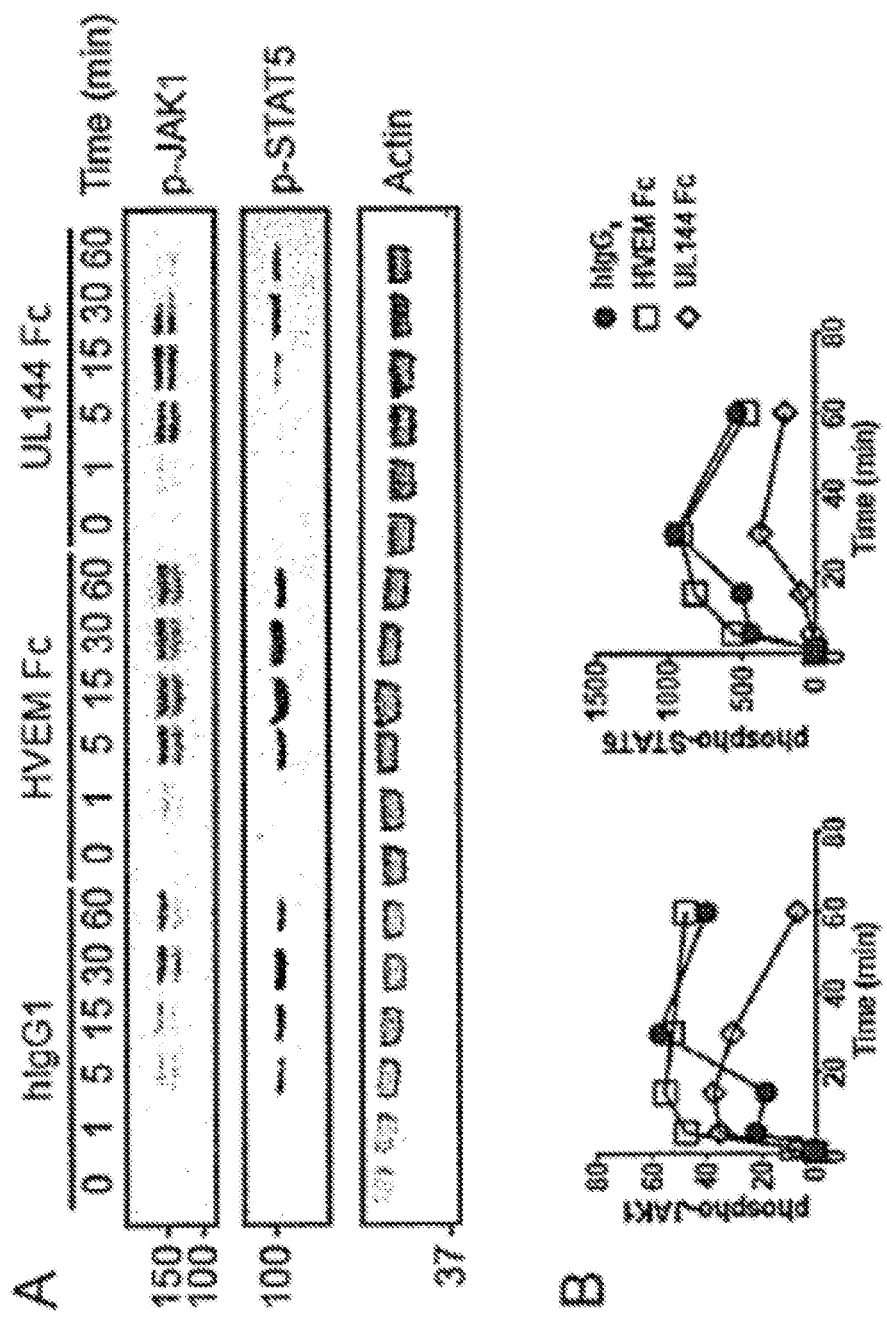
FIGS. 5A-B show selective BTLA agonists inhibit IL-2 signaling.
Figures 11A, 11B, 11C:
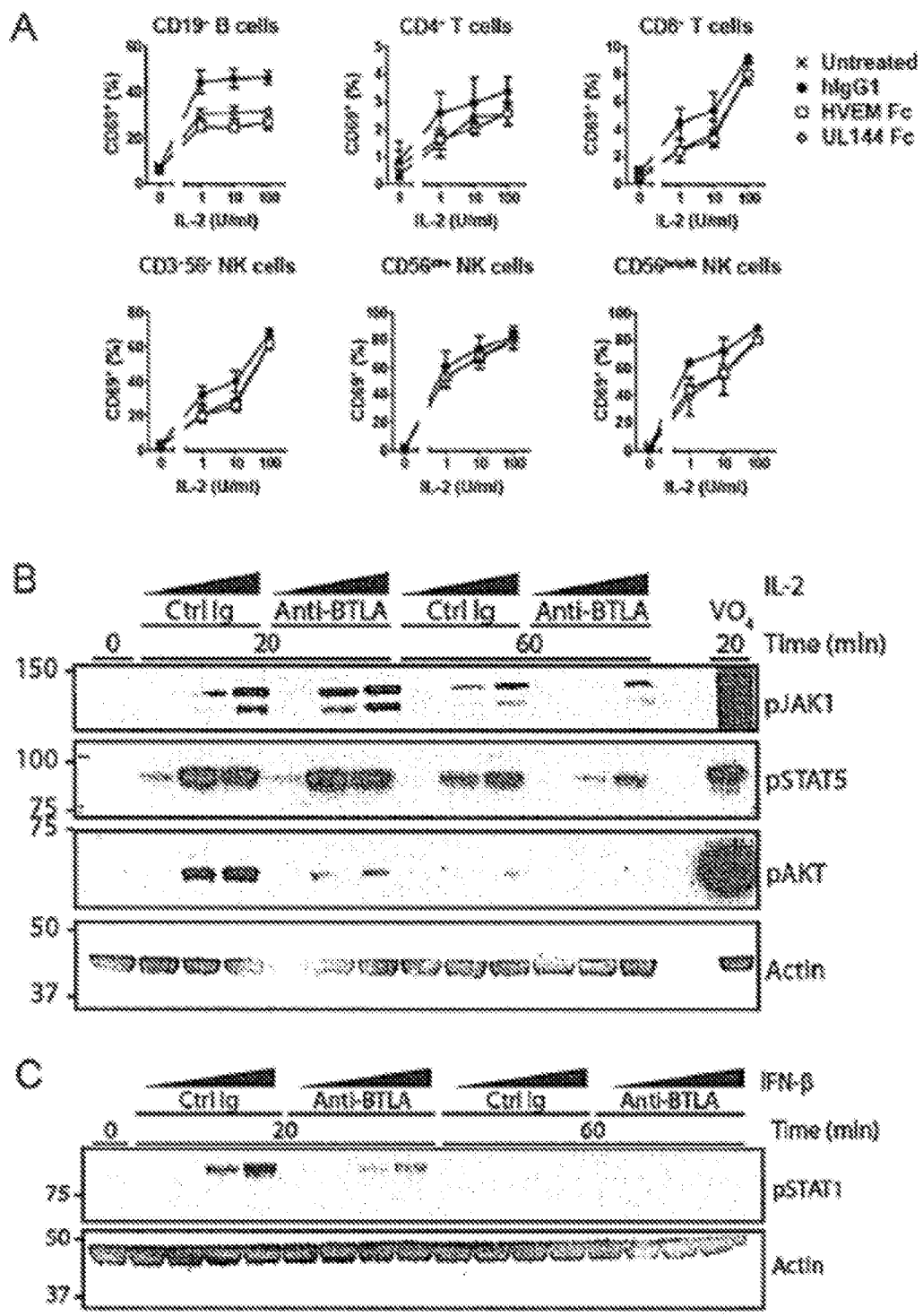
FIG. 11A are graphs showing the percent of CD69 expression in CD19+ B cells, CD4+ and CD8+ T cells, CD3+CD56+ cells, CD56dim and CD56bright NK cells in PBMC pretreated with the indicated Fc proteins.
FIG. 11B shows Western blots of NK92 cells were stimulated with titrated IL-2.
FIG. 11C shows Western blots of NK92 cells stimulated with titrated IFN-β.

It has been previously shown that in PBMC cultured with cytokines or CMV infected fibroblasts in vitro, soluble HVEM-Fc, but not UL144-Fc, uniquely co-stimulated activation of CD160-expressing NK cells. In parallel studies, inhibition of IL-2-induced CD69 expression by HVEM and UL144-Fc in diverse PBMC subsets was observed that correlated with the expression of BTLA (FIG. 11A). The capacity of cellular and viral HVEM to inhibit IL-2 signaling in the presence of CD160 was further examined (FIG. 5). The human NK cell line NK92 responds to IL-2 in a titratable fashion by phosphorylation of the kinase JAK1 leading to activation of STAT5, Akt and ERK pathways. In cells treated with IL-2 a decreased phosphorylation of JAK1, STAT5 and Akt proteins was observed following activation of BTLA with UL144-Fc or anti-BTLA mAb (clone MIH26), but not HVEM-Fc, indicating that UL144 targeting of BTLA was unhindered by the presence of excess CD160 (FIG. 5A, 5B and FIG. 11B). It was further tested whether BTLA regulated type I interferon signaling since this pathway is also regulated by SHP-1 inhibition. Anti-BTLA mAb (clone MIH26) reduced the magnitude of STAT1 phosphorylation at early and late times, demonstrating that in SHP-1 sensitive cytokine signaling pathways, BTLA exhibits broad inhibitory function (FIG. 11C). Additionally, CD160 limited HVEM, but not its viral mimic, from binding and activating BTLA. FIG. 11 shows PBMC pretreated with the indicated Fc proteins and stimulated with indicated concentrations of IL-2 for 6 hours prior to staining for CD69 expression within cellular subsets. Graphs show the percent of CD69 expression in CD19+ B cells, CD4+ and CD8+ T cells, CD3+ CD56+ cells, CD56dim and CD56bright NK cells. B.-C. NK92 cells were stimulated with titrated IL-2 (B.) and IFN-β (C.) at the indicated times after pretreating with anti-BTLA (MIH26) or control Ig. Western blots show whole cell extracts of phospho-JAK1, STAT5 and Akt (S473) to monitor IL-2 signaling, or phospho-STAT1 to monitor IFN-β signaling, and actin to control for total protein level Example 6

Bioengineered HVEM Selectively Activates BTLA Signaling

Figures 6A, 6B, 6C:
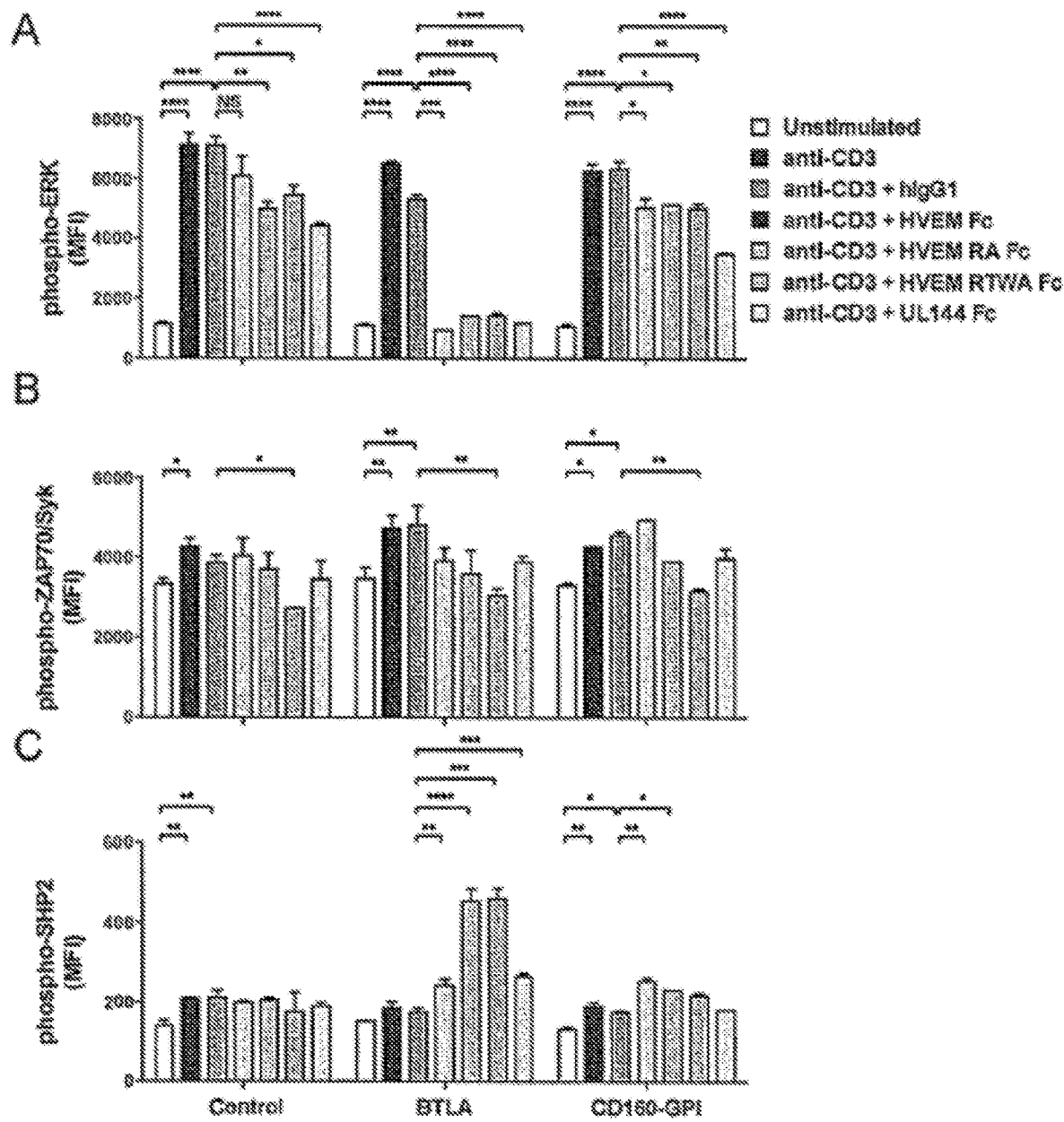
FIGS. 6A-C show that de novo mutant HVEM inhibits ZAP70/Syk activation.
Figures 12A, 12B:
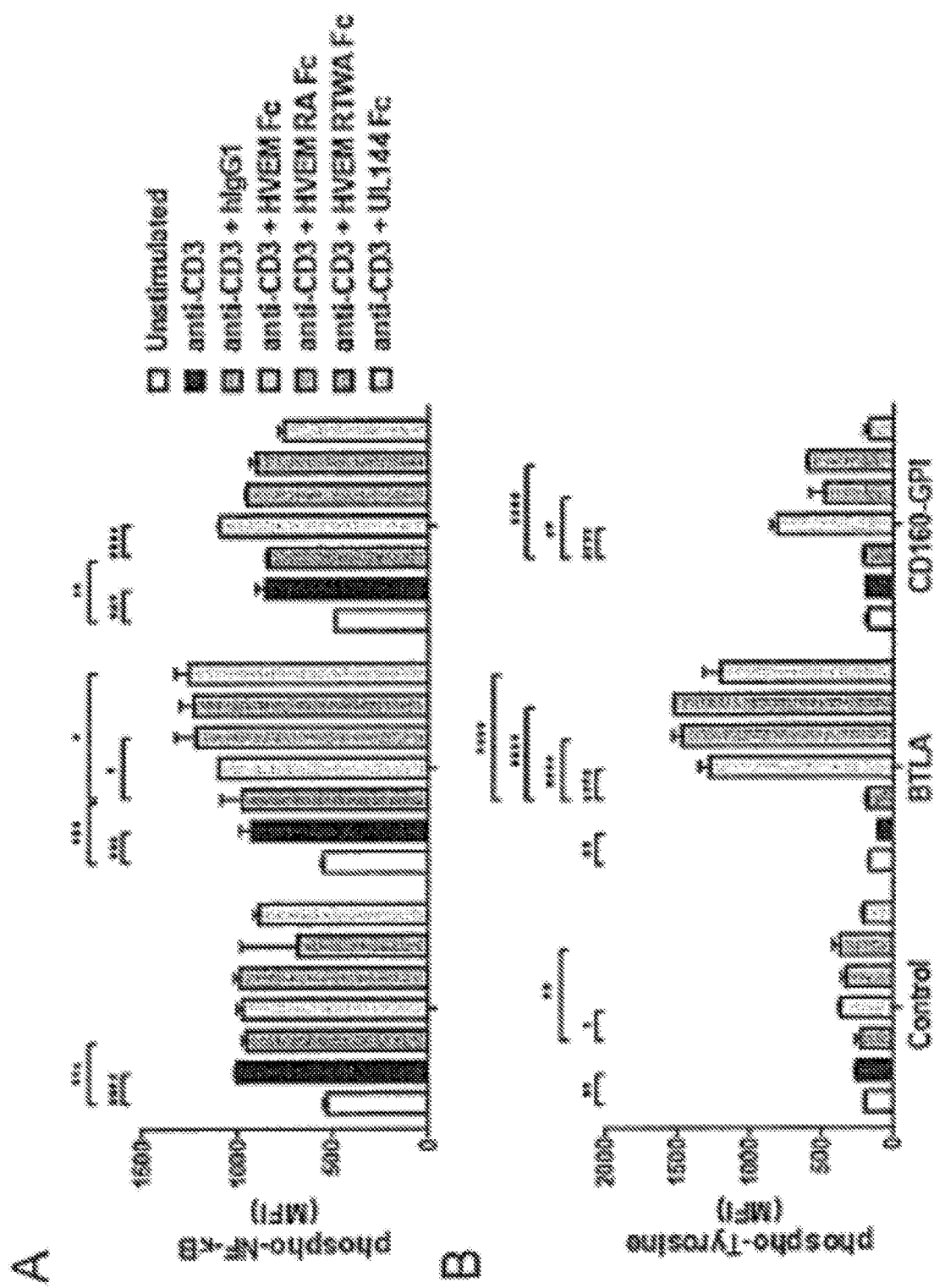
FIGS. 12A-B show JTAg cells transduced with the indicated HVEM ligands were cultured with microspheres coupled to anti-CD3 with or without Fc proteins.

The ligand binding selectivity of UL144 and the lymphoma mutations suggested that de novo engineering of HVEM should yield a BTLA specific agonist. Mutant HVEM-Fc proteins were engineered through alanine scanning, saturation, and combinatorial mutagenesis. It was found that HVEM muteins containing mutations at S58R and L90A (HVEM-RA) conferred selectivity for BTLA, while additional mutations at G68T and L70W enhanced BTLA affinity 10-fold (HVEM-RTWA). Notably, the RA and RTWA mutants both inhibited anti-CD3-induced phospho-ERK1/2 to a greater extent than parental HVEM-Fc proteins in control cells, and all HVEM-Fc proteins reduced ERK1/2 phosphorylation to background levels in cells ectopically expressing BTLA (FIG. 6A). Only the high affinity HVEM-RTWA mutant significantly reduced ZAP-70/Syk phosphorylation to background levels in all cells (FIG. 6B). In cells expressing ectopic BTLA, the inhibitory activity of the HVEM-RA and HVEM-RTWA mutants correlated with dramatic induction of phospho-SHP2 signals as well as total cellular phospho-tyrosine (FIG. 6C and FIG. 12B). Thus, the bioengineered HVEM-Fc reproduces selective and unhindered agonism of viral and mutant HVEM.

Example 7

Figures 13A, 13B, 13C, 13D, 13E, 13F, 13G:
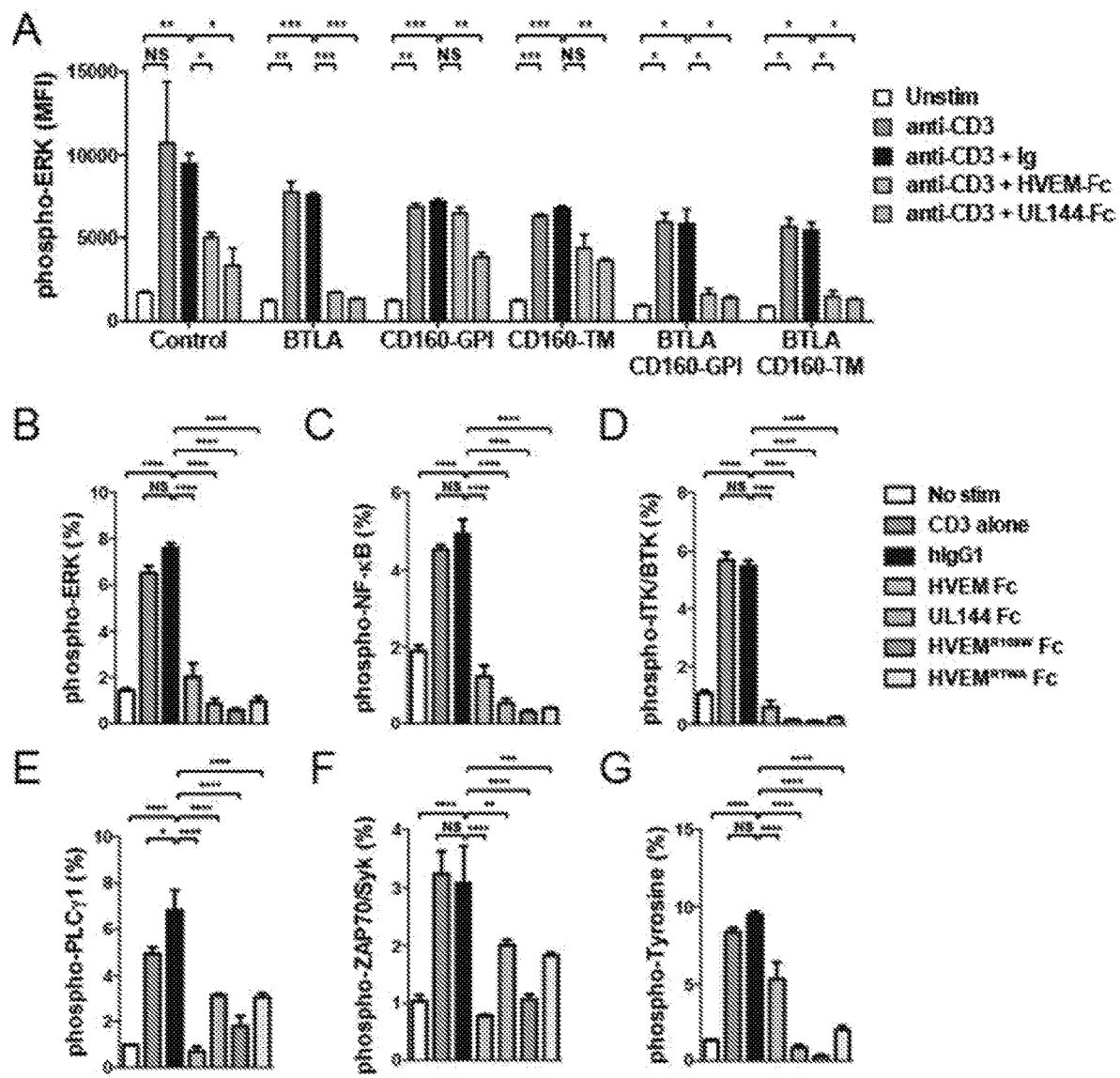
FIGS. 13A-B shows staining for phospho-ERK1/2 (T202/Y204).
FIG. 13C shows staining for phospho-NF-κB p65 (S529).
FIG. 13D shows staining for phospho-BTK/ITK (Y551/Y511).
FIG. 13E shows staining for phospho-PLCγ1 (Y783).
FIG. 13F shows staining for phospho-ZAP70/Syk (Y319/Y352)
FIG. 13G shows staining for phospho-tyrocino.

Diverse Pathogen-Associated and de Novo Bioengineered HVEM Mutein BTLA Agonists Inhibit T Cell Signaling HVEM mutein BTLA agonists were shown to inhibit T cell signaling. JTAg cells were transduced with the control BTLA, CD160-GPI, CD160-TM, BTLA CD160-GPI and BTLACD160-TM HVEM ligands by electroporation and allowed to rest for 48 hours prior to activation, or were stably transduced with retroviruses expressing the indicated HVEM ligands. To activate JTAg, cells aldehyde sulfate microspheres were coupled with anti-CD3 at 100 µg/ml with or without the indicated HVEM or UL144 Fc proteins at 1 µM in PBS for 90' at 37° C. Microspheres were washed twice and incubated at a 4:1 microsphere to cell ratio with JTAg cells for 5 minutes. Cells were immediately fixed with 2% paraformaldehyde, permeabilized with 90% methanol, and stained with the indicated phospho-specific antibodies. Cells were then examined for intracellular staining of phospho-ERK1/2 (T202/Y204) (FIG. 13A., B.), phospho-NF-κB p65 (S529) (FIG. 13C.), phospho-BTK/ITK (Y551/Y511) (FIG. 13D.), phospho-PLCγ1 (Y783) (FIG. 13E.), phospho-ZAP70/Syk (Y319/Y352) (FIG. 13F.), and phospho-tyrosine (FIG. 13G.). FIG. 13A shows graphs of the MFI of stained cells. FIGS. 13A.-G. show the percent positive of stained cells. (mean±SEM representative of three experiments). *, $p<0.05$; , $p<0.01$; *, $p<0.001$; ****, $p<0.0001$.

Example 8

BTLA Agonists Inhibit B Cell Signaling

Figures 14A, 14B:
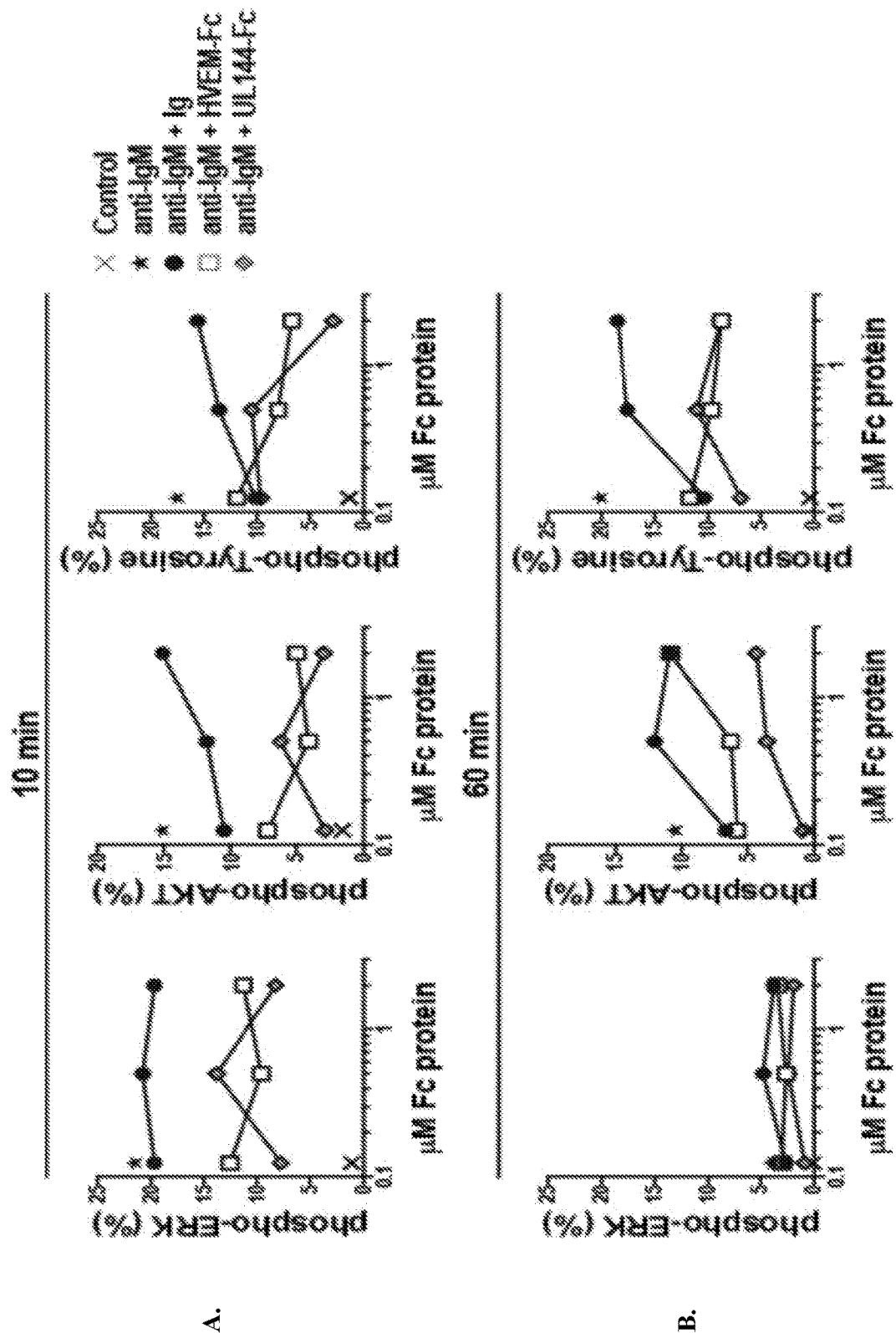
FIGS. 14A-B show that BTLA agonists inhibit B cell signaling. BJAB cells were cultured with microspheres coupled to anti-IgM with or without titrated Fc proteins.

BTLA agonists were shown to inhibit B cell signaling. To activate BJAB cells aldehyde sulfate microspheres were coupled with anti-IgM at 100 µg/ml with or without the indicated HVEM or UL144 Fc proteins at 1 µM in PBS for 90' at 37° C. Microspheres were washed twice and incubated at a 4:1 microsphere to cell ratio with BJAB cells for 10 or 60 minutes. Cells were immediately fixed with 2% paraformaldehyde, permeabilized with 90% methanol, and stained with the indicated phospho-specific antibodies. BJAB cells were then examined for intracellular staining of phospho-ERK1/2 (pT202/pY204), phospho-Akt (S473), or phospho-tyrosine (FIG. 14A-B). FIGS. 14A-B show the percent of cells positive for phospho-ERK1/2 (pT202/pY204), phospho-Akt (S473), or phospho-tyrosine.

Figures 15A, 15B, 15C, 15D:
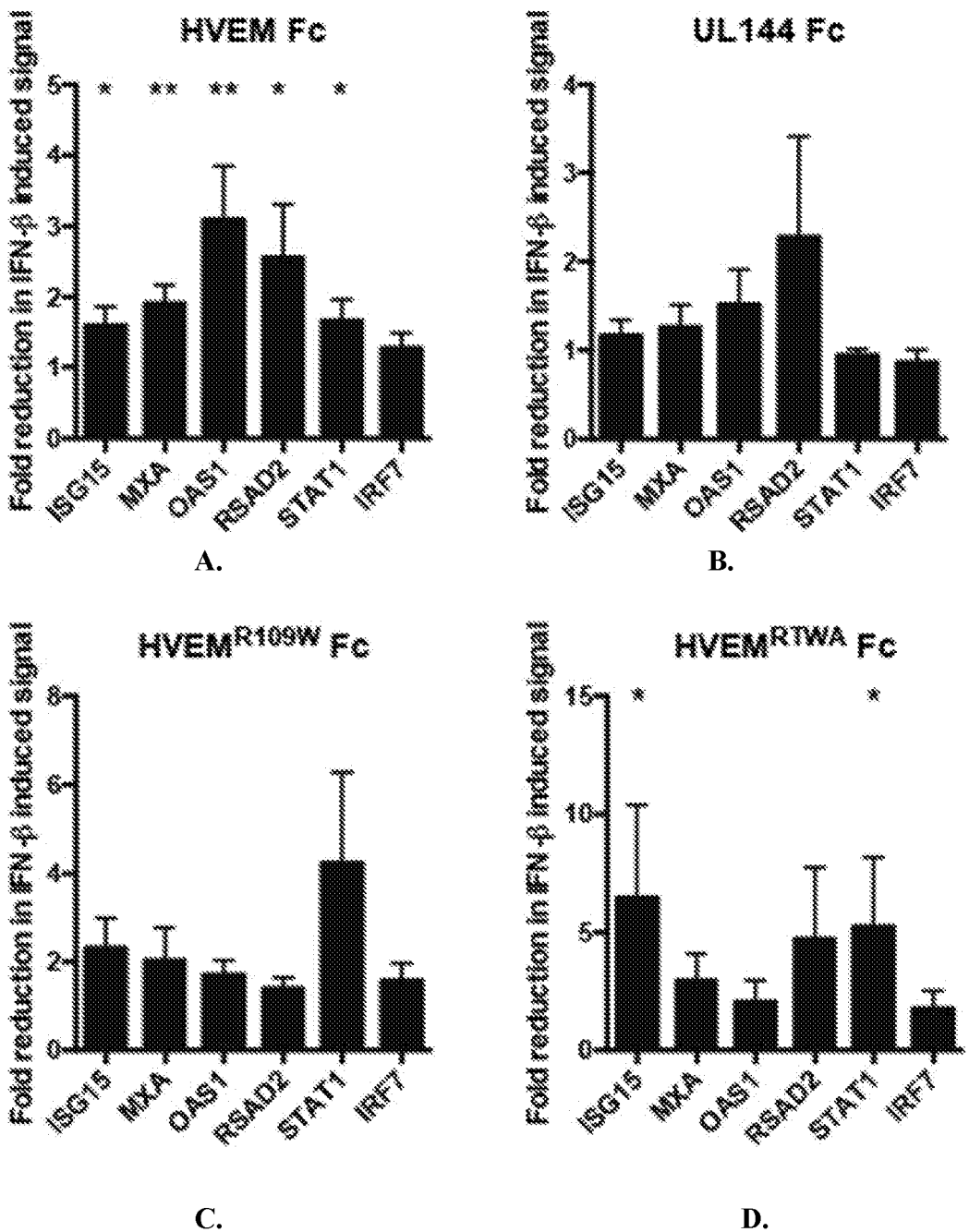
FIGS. 15A-D show that BTLA agonists inhibit interferon activation of B cells. Human B cells stimulated with interferon-β in the presence of microspheres coupled to control immunoglobulin or BTLA agonist fusion proteins.

BTLA agonists inhibit interferon activation of B cells. To activate human B cells aldehyde sulfate microspheres were coupled with the indicated HVEM or UL144 Fc proteins at 1 µM in PBS for 90' at 37° C. Microspheres were washed twice and incubated at a 4:1 microsphere to cell ratio with human B cells purified from normal human donor blood PBMC, and stimulated with 10 U/ml interferon-β for 6 hours prior to lysis and RNA isolation. FIG. 15 shows the fold reduction in the levels of each of the indicated interferon stimulated genes when cells were treated with each of the BTLA agonists (HVEM, UL144 Fc, HVEM$^{R109W}$ Fc and HVEM$^{RTWA}$ Fc) compared to control. (mean±SEM, pooled data from two experiments). *, $p<0.05$; **, $p<0.01$.

Figure 16A:
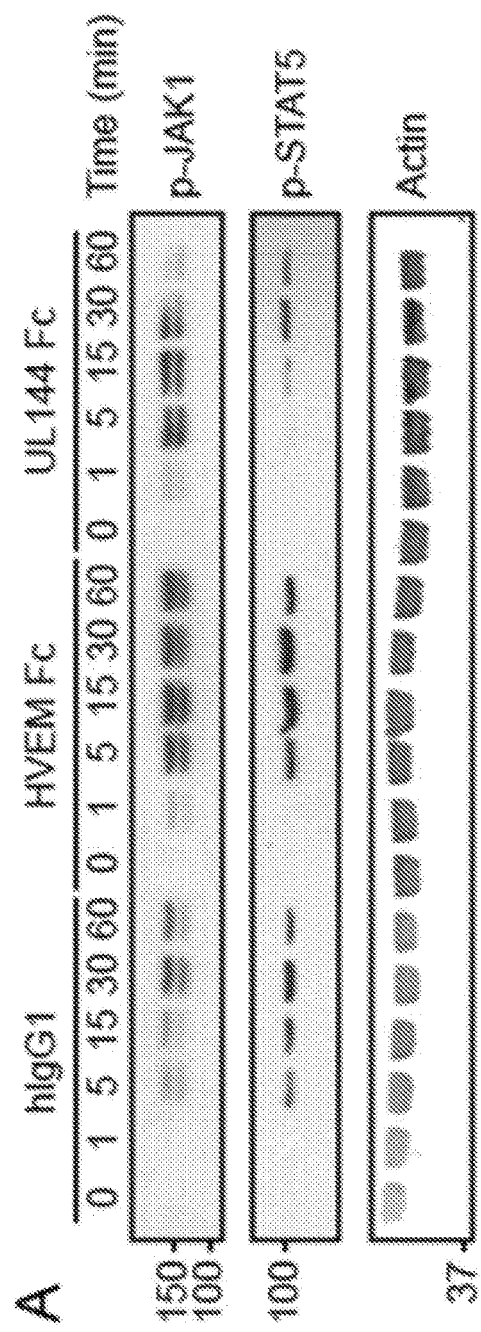
FIGS. 16A-B show that selective BTLA agonists limit IL-2 signaling in NK cells.
Figure 16B:
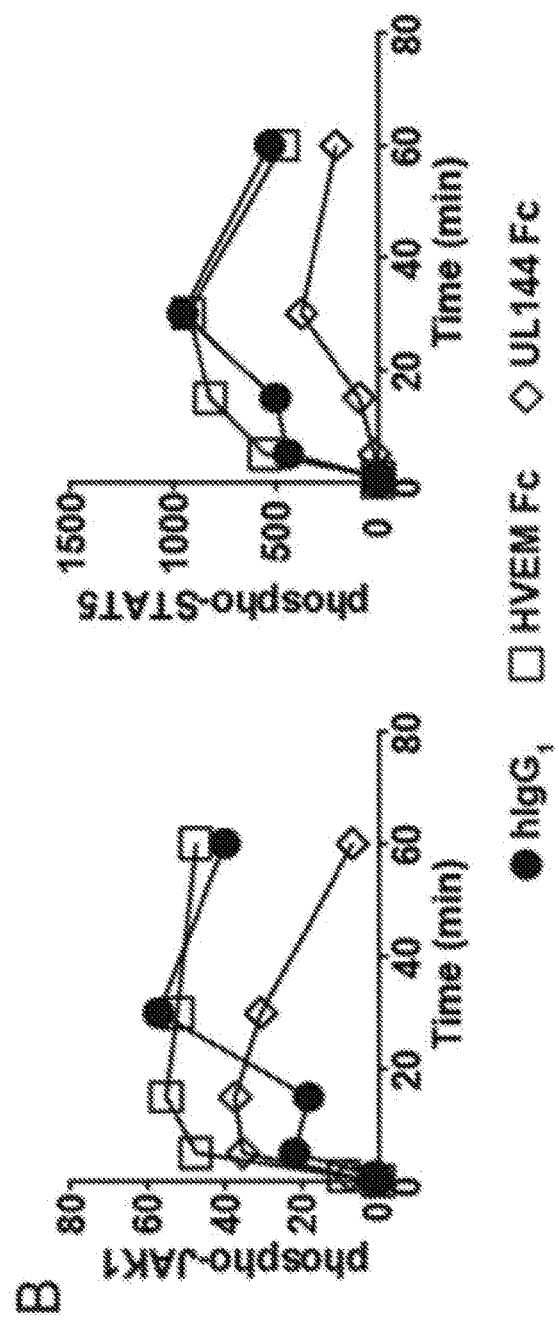

BTLA agonists were found to limit IL-2 signaling in NK cells. NK92 cells were cultured without serum for at least four hours, and then stimulated with 20 U/ml of human IL-2 at 0, 1, 5, 15, 30 and 60 minutes after pretreating with the indicated Fc and antibodies at 2 µg/ml on ice for 15 minutes (FIG. 16). After activation cells were lysed in RIPA buffer and protein phosphorylation was analyzed by Western blot. FIG. 16A shows Western blots of whole cell extracts of phospho-JAK1, phospho-STAT5, and actin to control for total protein levels. FIG. 16B shows graphs indicating the quantitation of band intensity normalized to actin.

Example 9

Identification of Ligand Selectivity in Mouse HVEM

Figures 17A, 17B, 17C:
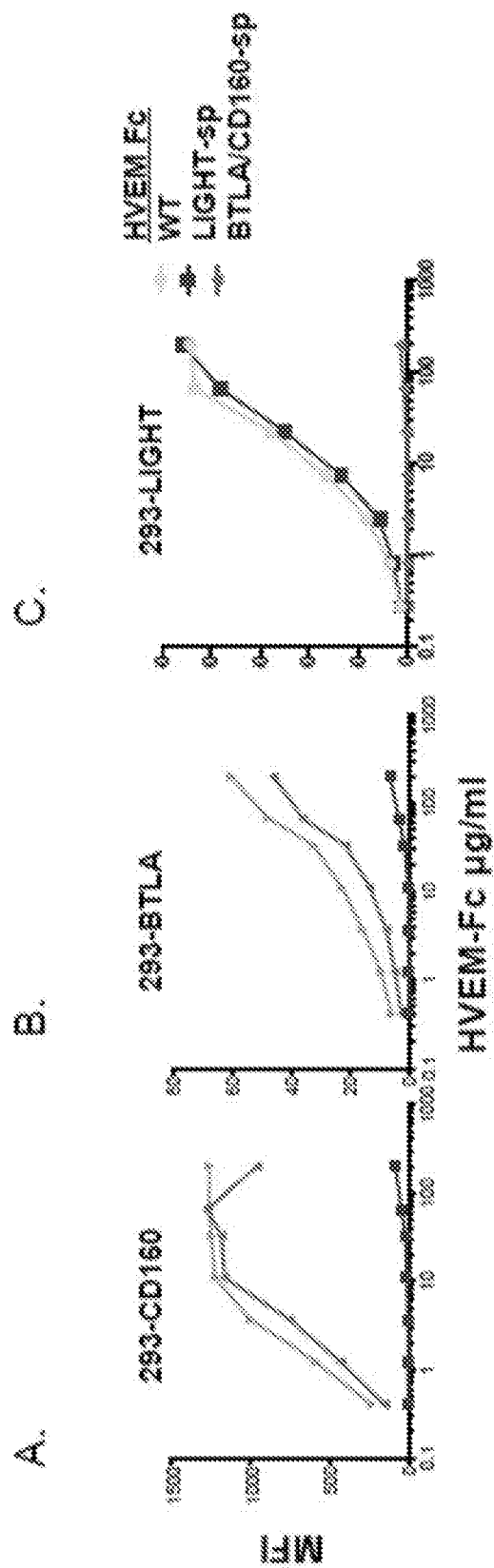
FIGS. 17A-C show the identification of ligand selectivity in mouse HVEM. HVEM-Fc muteins including variants that either blocked binding to LIGHT (BTLA/CD160-sp) or both BTLA and CD160 (LIGHT-sp) were titrated onto 293T cells.

Selectivity of ligands was determined in mouse HVEM. A panel of mouse HVEM-Fc muteins were produced by transient transfection into 293T cells including wild-type HVEM, and two variants containing single amino acid changes that were predicted to block binding to LIGHT (BTLA/CD160-sp) or both BTLA and CD160 (LIGHT-sp) based on homology to human HVEM (FIG. 17). HVEM-Fc proteins were titrated onto 293T cells transiently transfected with either mouse CD160 (FIG. 17A), mouse BTLA (FIG. 17B), and mouse LIGHT, and binding was detected using anti-human Fc. Specific binding measured in flow cytometric analysis (FIG. 17C). The graphs show MFI of staining of HVEM-Fc proteins onto ligand expressing cells.

Example 10

Selective HVEM-Fc Inhibits Skin Inflammation In Vivo

Figures 18A, 18B, 18C:
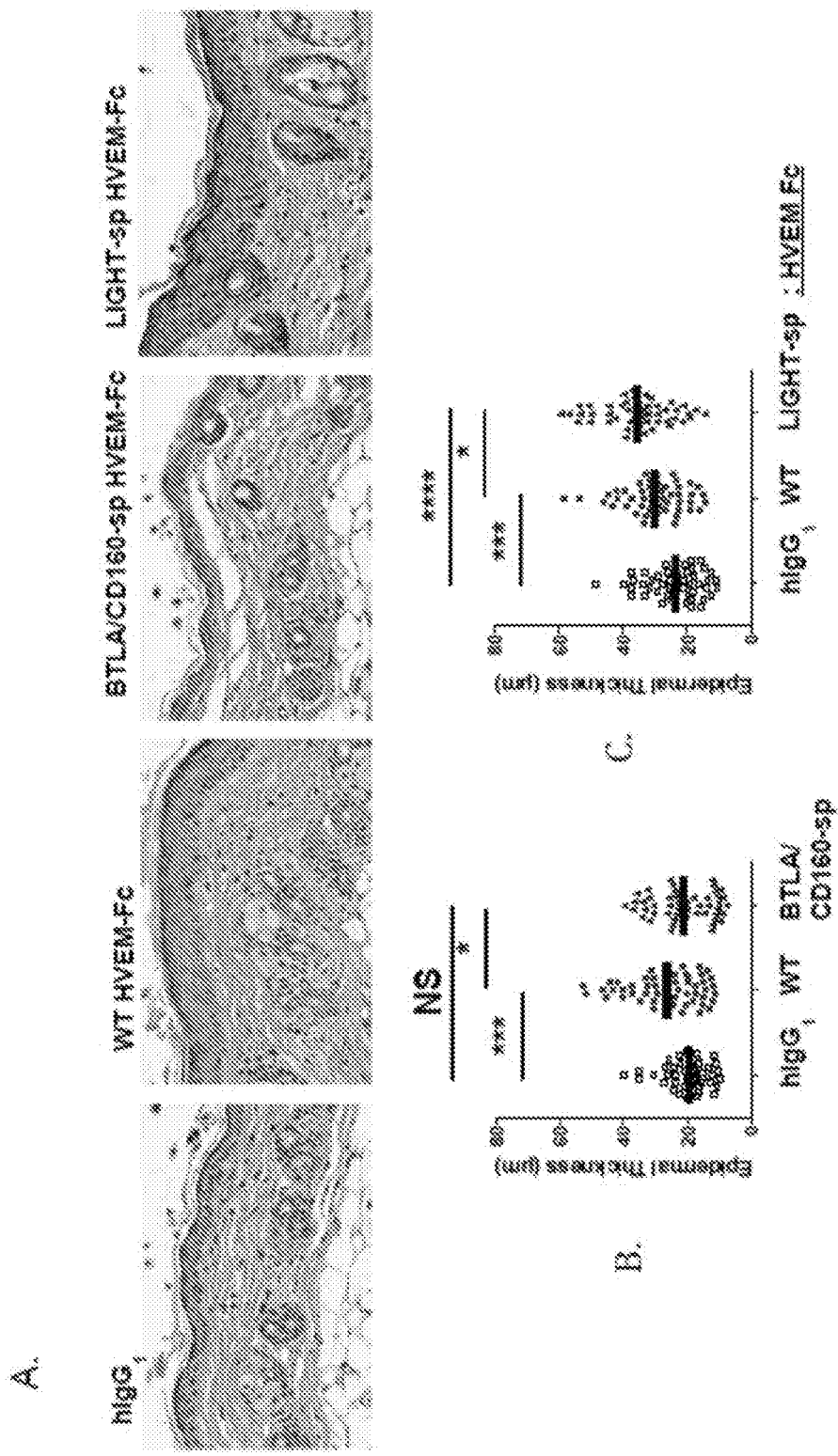
FIGS. 18A-C show that selective HVEM-Fc inhibits skin inflammation in vivo. Mouse HVEM-Fc muteins were injected intraperitoneally into imiquimod treated animals as a model of skin inflammation.

A HVEM-Fc was shown to inhibit skin inflammation in vivo. Mouse HVEM-Fc muteins were injected intraperitoneally into imiquimod treated animal models of skin inflammation. Skin tissue was harvested after three applications of imiquimod (Aldara formulation) at 50 mg on the shaved backs of each animal on each day of treatment, and sectioned for histological analysis. Epidermal thickness was quantitated in H & E stained skin sections at 10 sites over the length of each tissue. Representative images show epidermal thickening in different animal groups treated with HVEM muteins (FIG. 18A). FIG. 18B shows quantitation of epidermal thickness. *, $p<0.05$; , $p<0.01$; *, $p<0.001$; ****, $p<0.0001$.

Example 11

Summary

The data presented herein show that virus and cancer cell expression of BTLA selective agonists is a common strategy to target the HVEM signaling network. Virus evolution and mutations in HVEM that avoid CD160 binding appear to provide a selective advantage for the pathogen and cancer cell. It is shown that the activity of the viral HVEM mimic in CMV is unhindered in CD160-expressing cells compared to HVEM, directly inhibiting the activation of ZAP70/Syk and downstream ERK1/2 pathways following antigen receptor stimulation in lymphocytes. Additionally, in CD160-expressing NK cells the activation of BTLA by the viral HVEM mimic directly limits inflammatory cytokine signaling. Together, these data illustrate how the potential to limit inflammatory signaling by inhibitory receptors can provide a selective pressure for diverse intracellular pathogens such as viruses and tumors. This knowledge base of viral and tumor mutations prompted bioengineering of HVEM to achieve selectivity and high affinity for BTLA, which may show utility in altering inflammatory and proliferative processes.

The UL144 protein was initially modeled using the solved structure of HVEM in part because of their homology (FIG. 1A). However, there are subtle binding differences between UL144 and HVEM to certain BTLA mutants, to BTLA bound to the 6F4 antibody, and to BTLA in cis indicated non-identical interactions (FIG. 3, 4). UL144 could not be reverted to a CD160-binding protein through individual point mutation, likely reflecting multiple specificity changes that arose during virus-host evolution. As a result the UL144 protein is highly antigenic despite retention of BTLA binding across strains. In contrast, tumor-associated HVEM each contain only one mutation that alone could not abolish all CD160 binding. There are other examples of TNF receptors interacting with Ig domains for example, NGFRp75 with Longo1. Notably HVEM itself was initially identified through its interaction with the Ig domain of Herpes simplex virus glycoprotein D. CMV expresses another protein, ORF UL141, which binds TNF-related apoptosis inducing ligand receptors (TRAIL-R). The co-complex of these two proteins was recently solved showing that UL141 folds as an Ig domain, however, contact between these proteins occurs on the surface where the ligand TRAIL engages TRAIL-R, distinct from HVEM interactions with BTLA or CD160. HVEM may be unique in adopting several protein species of ligands, and complexes between the N-terminal cysteine rich domain 1 (CRD1) of TNFR proteins and Ig domains do not appear to be a favored type of protein-protein interaction among eukaryotes. It is interesting to note more frequent use of these unconventional interactions by diverse viruses, leading to the tempting suggestion that modulating immune receptors may enhance pathogen survival.

It was found that BTLA inhibited IL-2 and type I interferon signaling in human NK cells and confirmed the role of BTLA as an immune checkpoint inhibitor regulating T and B cell receptor signaling. The mechanism of inhibitory signaling downstream of BTLA is thought to include activation of SHP-1 or 2, and likely involves additional pathways. The inhibitory effect of bioengineered HVEM-RTWA on ZAP70/Syk phosphorylation is consistent with previous studies demonstrating that CD3ζ and Syk are direct targets of BTLA activity in T and B cells. JAK/STAT signaling is regulated in part by the activation of SHP-1 and dephosphorylation of target proteins including JAK kinases and STAT proteins. BTLA agonists may directly target cytokine signaling through SHP-1 recruitment or through the engagement of unknown inhibitory pathways.

In contrast to selective virus and mutant BTLA agonists, HVEM interacts with BTLA, LIGHT, and CD160 in activated T cells, while in NK cells the abundant expression of CD160 sequesters HVEM, potentially activating pro-inflammatory signaling. In the context of lymphoma mutated TNFRSF14 is often paired with a non-functional allele, resulting in worse prognosis. The above described experiments predict that HVEM mutation away from CD160 binding prevents activation of cytolytic cells, while retention of BTLA binding activates inhibitory signaling in neighboring cells. The identification of DLBCL deletions in LIGHT and BTLA, both of which can activate HVEM signaling in trans, further supports the hypothesis that a major selective factor is the activation of tumor infiltrating lymphocytes. Additionally, tumors themselves may respond to LIGHT and BTLA to activate survival signals downstream of HVEM. Notably, follicular T helper cells prominently express BTLA and LIGHT, and may contribute to maintenance of HVEM functionality within lymphoma. Continued investigation is warranted to determine how HVEM contributes to lymphoma fitness in the tumor microenvironment through ligand selection. The expression of BTLA, LIGHT, and CD160 varies greatly between different cell types, activation, and differentiation states. Thus dynamic regulation of HVEM ligands provides a mechanism for control of activating and inhibitory signals depending on cellular context. The determination of factors regulating receptor and ligand expression will allow for a better understanding of the role of these proteins in immune responses, and how these pathways can be manipulated for therapeutic intervention. The development of targeted agonists to BTLA or other inhibitory receptors may serve to increase the repertoire of treatments for inflammatory disease.

Although the invention has been described with reference to the above examples, it will be understood that modifications and variations are encompassed within the spirit and scope of the invention. Accordingly, the invention is limited only by the following claims.

TABLE 1

| Primers used for cloning and site directed mutagenesis | | | SEQ ID |
|---|---|---|---|
| Gene | Primer | Sequence | NO: |
| | Human CMV UL144 | | |
| E27A Mutant | Fiala UL144 E46 For | AAACCCGAAGCAGTGCAATTAGGAAATCAGTG | 3 |
| E27A Mutant | Fiala UL144 E46 Rev | TAATTGCACTGCTTCGGGTTTGCATATTTCAG | 4 |
| V28Y Mutant | UL144_V28YTop | ACCCGAAGAATATCAATTAGGAAATCAGTGTTGTC | 5 |
| V28Y Mutant | UL144_V28YBot | TTCCTAATTGATATTCTTCGGGTTTGCATATTTC | 6 |
| Q29P Mutant | UL144_Q29PTop | GAAGAAGTGCCATTAGGAAATCAGTGTTGTCCC | 7 |
| Q29P Mutant | UL144_Q29PBot | ATTTCCTAATGGCACTTCTTCGGGTTTGCATATTTC | 8 |
| N32S Mutant | UL144_N32STop | GCAATTAGGAAGTCAGTGTTGTCCCCCATGTAAAC | 9 |
| N32S Mutant | UL144_N32SBot | ACAACACTGACTTCCTAATTGCACTTCTTCGG | 10 |
| Q33A Mutant | Fiala UL144 Q52 For | TTAGGAAATGCGTGTTGTCCCCCATGTAAACAAG | 11 |
| Q33A Mutant | Fiala UL144 Q52 Rev | GGGACAACACGCATTTCCTAATTGCACTTCTTC | 12 |
| P36A Mutant | Fiala UL144 P55 For | CAGTGTTGTGCCCCATGTAAACAAGGATATCGTG | 13 |

TABLE 1-continued

Primers used for cloning and site directed mutagenesis

| Gene | Primer | Sequence | SEQ ID NO: |
|---|---|---|---|
| P36A Mutant | Fiala UL144 P55 Rev | TTTACATGGGGCACAACACTGATTTCCTAATTG | 14 |
| P37K Mutant | UL144_P37KTop | GTGTTGTCCCAAATGTAAACAAGGATATCGTGTTAC | 15 |
| P37K Mutant | UL144_P37KBot | TTGTTTACATTTGGGACAACACTGATTTCCTAATTG | 16 |
| K39S Mutant | K39STop | TCCCCCATGTTCACAAGGATATCGTTTACAGG | 17 |
| K39S Mutant | K39SBot | ATATCCTTGTGAACATGGGGGACAACACTGATTTC | 18 |
| G41A Mutant | Fiala UL144 G60 For | TGTAAACAAGCATATCGTGTTACAGGACAATGTAC | 19 |
| G41A Mutant | Fiala UL144 G60 Rev | AACACGATATGCTTGTTTACATGGGGGCAACACTG | 20 |
| Y42A Mutant | UL144F-Y42A-F | CCCCCATGTAAACAAGGAGCTCGTGTTACAGGACAATG | 21 |
| Y42A Mutant | UL144F-Y42A-R | CATTGTCCTGTAACACGAGCTCCTTGTTTACATGGGG | 22 |
| R43A Mutant | Fiala UL144 R62A For | CAAGGATATGCTGTTACAGGACAATGTACGCAATATAC | 23 |
| R43A Mutant | Fiala UL144 R62A Rev | TCCTGTAACAGCATATCCTTGTTTACATGGGGG | 24 |
| T45A Mutant | Fiala UL144 T64 For | TATCGTGTTGCAGGACAATGTACGCAATATACG | 25 |
| T45A Mutant | Fiala UL144 T64 Rev | ACATTGTCCTGCAACACGATATCCTTGTTTACATGG | 26 |
| G46A Mutant | Fiala UL144 G65 For | CGTGTTACAGCACAATGTACGCAATATACGAGTAC | 27 |
| G46A Mutant | Fiala UL144 G65 Rev | CGTACATTGTGCTGTAACACGATATCCTTGTTTAC | 28 |
| G46K Mutant | FUL144-G46K 5' | AAACAAGGATATCGTGTTACAAAACAATGTACGCAATATACGAGT | 29 |
| G46K Mutant | FUL144-G46K 3' | ACTCGTATATTGCGTACATTGTTTTGTAACACGATATCCTTGTTT | 30 |
| Q47A Mutant | UL144_Q47ATop | GTTACAGGAGCATGTACGCAATATACGAGTACAAC | 31 |
| Q47A Mutant | UL144_Q47ABot | TGCGTACATGCTCCTGTAACACGATATCCTTG | 32 |
| T49G Mutant | UL144_T49GTop | GGACAATGTGGGCAATATACGAGTACAACATGTAC | 33 |
| T49G Mutant | UL144_T49GBot | CGTATATTGCCCACATTGTCCTGTAACACGATATC | 34 |
| Q50A Mutant | Fiala UL144 Q69 For | CAATGTACGGCATATACGAGTACAACATGTACAG | 35 |
| Q50A Mutant | Fiala UL144 Q69 Rev | ACTCGTATATGCCGTACATTGTCCTGTAACACGATATC | 36 |
| T52A Mutant | Fiala UL144 T71 For | ACGCAATATGCGAGTACAACATGTACACTTTGCCC | 37 |
| T52A Mutant | Fiala UL144 T71 Rev | TGTTGTACTCGCATATTGCGTACATTGTTCTGTAAC | 38 |
| N61A Mutant | UL144_N61ATop | CTTTGCCCTGCCGGTACGTATGTATCAGGGC | 39 |
| N61A Mutant | UL144_N61ABot | CGTACCGGCAGGGCAAAGTGTACATGTTGTAC | 40 |
| L68A Mutant | Fiala UL144 L86 For | GTATCAGGGGCTTACAATTGTACCAATTGCACTG | 41 |
| L68A Mutant | Fiala UL144 L86 Rev | ACAATTGTAAGCCCCTGATACATACGTACCGTTAG | 42 |
| E76M Mutant | UL144_E76MTop | CAATTGCACTATGTGTAATGACACTGAGGTTAC | 43 |
| E76M Mutant | UL144_E76MBot | CAATTGCACTATGTGTAATGACACTGAGGTTAC | 44 |
| P106A Mutant | Fiala UL144 P124 For | TTTTCCGTTGCAGGCGTCCAACATCACAAGCAACG | 45 |
| P106A Mutant | Fiala UL144 P124 Rev | TTGGACGCCTGCAACGGAAAATGACGTATAATTC | 46 |
| Human HVEM | | | |
| P59S Mutant | hHVEM_P59STop | CAAGTGCAGTTCAGGTTATCGTGTGAAGGAG | 47 |
| P59S Mutant | hHVEM_P59SBot | CGATAACCTGAACTGCACTTGGGGCAGCAC | 48 |
| G60D Mutant | HuHVEMG60Dfor | tgcagtccagattatcgtgtgaaggaggcctg | 49 |
| G60D Mutant | HuHVEMG60Drev | ACACGATAATCTGGACTGCACTTGGGGC | 50 |
| Y61C Mutant | HuHVEMY61Cfor | GTCCAGGTTGTCGTGTGAAGGAGGCCTGC | 51 |
| Y61C Mutant | HuHVEMY61Crev | CTTCACACGACAACCTGGACTGCACTTGGG | 52 |
| G72D Mutant | hHVEM_G72DTop | GCTGACGGACACAGTGTGTGAACCCTGC | 53 |
| G72D Mutant | hHVEM_G72DBot | ACACACTGTGTCCGTCAGCTCCCCGCAG | 54 |
| T82P Mutant | hHVEM_T82PTop | TCCAGGCCCCTACATTGCCCACCTCAATG | 55 |
| T82P Mutant | hHVEM_T82PBot | AATGTAGGGGCCTGGAGGGCAGGGTTC | 56 |
| Ins91I Mutant | hHVEM_ins9ITop | CTCAATGGCCTAATAAGCAAGTGTCTGCAGTGC | 57 |
| Ins91I Mutant | hHVEM_ins9IIBot | CACTTGCTTATTAGGCCATTGAGGTGGGCAATG | 58 |
| A102P Mutant | hHVEM_A102PTop | GTGACCCACCCATGGGCCTGCGCGCG | 59 |
| A102P Mutant | hHVEM_A102PBot | GGCCCATGGGTGGGTCACACATTTGGCACTG | 60 |
| R109W Mutant | HuHVEMR109Wfor | CGCGAGCTGGAACTGCTCCAGGACAGAG | 61 |
| R109W Mutant | HuHVEMR109Wrev | GAGCAGTTCCAGCTCGCGCGCAGGCCC | 62 |
| Human BTLA | | | |
| Q37A Mutant | HuBTLAQ37Atop | catgtgatgtAGCGCTTTATATAAAGAGACAATCTGAACACTC | 63 |
| Q37A Mutant | HuBTLAQ37Abot | CTTTATATAAAGCGCTACATCACATGATTCTTTCCCATG | 64 |
| L38H Mutant | HuBTLAL38Htop | ATGTGATGTACAGCATTATATAAAGAGACAATCTGAACACTCC | 65 |
| L38H Mutant | HuBTLAL38Hbot | TTGTCTCTTTATATAATGCTGTACATCACATGATTCTTTCC | 66 |
| R42D Mutant | HuBTLAR42Dtop | CTTTATATAAAGGACCAATCTGAACACTCCATCTTAGC | 67 |
| R42D Mutant | HuBTLAR42Dbot | GTGTTCAGATTGGTCCTTTATATAAAGCTGTACATCACATGATTC | 68 |
| E45A Mutant | HuBTLAE45Atop | AGAGACAATCTGCACACTCCATCTTAGCAGGAGATCC | 69 |
| E45A Mutant | HuBTLAE45Abot | AAGATGGAGTGTGCAGATTGTCTCTTTATATAAAGCTGTAC | 70 |
| E57A Mutant | HuBTLAE57Atop | CTTTGAACTAGCATGCCCTGTGAAATACTGTGCTAAC | 71 |
| E57A Mutant | HuBTLAE57Abot | TCACAGGGCATGCTAGTTCAAAGGGATCCTGCTAAG | 72 |
| P59A Mutant | HuBTLAP59Atop | GAACTAGAATGCGCTGTGAAATACTGTGCTAACAGGC | 73 |
| P59A Mutant | HuBTLAP59Abot | GTATTTCACAGCGCATTCTAGTTCAAAGGATCTC | 74 |
| K90A Mutant | HuBTLAK90Atop | ACAAGTTGGGCGGAAGAGAAGAACATTTCATTTTTCATTC | 75 |
| K90A Mutant | HuBTLAK90Abot | CTTCTCTTCCGCCCAACTTGTTTGTCTATCTTCAAGTTTTAC | 76 |
| V117A Mutant | HuBTLAV117Atop | TGTTCTGCAAATTTTCAGTCTAATCTCATTGAAAGC | 77 |
| V117A Mutant | HuBTLAV117Abot | GATTAGACTGAAAATTTGCAGAACAGCGGTATGACCC | 78 |
| N118F Mutant | HuBTLAN118Ftop | GCTGTTCTGCATTTTTCAGTCTAATCTCATTGAAAGC | 79 |
| N118F Mutant | HuBTLAN118Fbot | TAGACTGAAAAATGCAGAACAGCGGTATGAC | 80 |
| F119A Mutant | HuBTLAF119Atop | GTTCTGCAAATGCTCAGTCTAATCTCATTGAAAGCCAC | 81 |
| F119A Mutant | HuBTLAF119Abot | GAGATTAGACTGAGCATTTGCAGAACAGCGGTATG | 82 |
| S121H Mutant | HuBTLAS121Htop | CAAATTTTCAGCATAATCTCATTGAAAGCCACTCAAC | 83 |

TABLE 1-continued

Primers used for cloning and site directed mutagenesis

| Gene | Primer | Sequence | SEQ ID NO: |
|---|---|---|---|
| S121H Mutant | HuBTLAS121Hbot | CAATGAGATTATGCTGAAAATTTGCAGAACAGCG | 84 |
| H127D Mutant | HuBTLAH127Dtop | CATTGAAAGCGACTCAACAACTCTTTATGTGACAGATG | 85 |
| H127D Mutant | HuBTLAH127Dbot | GTTGTTGAGTCGCTTTCAATGAGATTAGACTGAAAATTTG | 86 |
| S128H Mutant | HuBTLAS128Htop | TGAAAGCCACCATACAACTCTTTATGTGACAGATGTAAAAAG | 87 |
| S128H Mutant | HuBTLAS128Hbot | AAGAGTTGTATGGTGGCTTTCAATGAGATTAGACTG | 88 |

TABLE S2

Monovalent and bivalent kinetic rate constants for Fc fusion protein binding

| | Analyte | |
|---|---|---|
| | HVEM-Fc | HuCMV UL144-Fc |
| Monovalent Analysis | | |
| $k_a$ ($\times 10^4$ $M^{-1}s^{-1}$) | 3.74 | 1.61 |
| $k_d$ ($\times 10^{-3}$ $s^{-1}$) | 6.6 | 4.76 |
| $K_D$ (nM) | 177 | 295 |
| Bivalent Analysis | | |
| $k_{a1}$ ($\times 10^4$ $M^{-1}s^{-1}$) | 1.53 | 0.781 |
| $k_{d1}$ ($\times 10^{-3}$ $s^{-1}$) | 9.02 | 5.1 |
| $k_{a2}$ ($\times 10^{-3}$ $M^{-1}s^{-1}$) | 57.3 | 0.0139 |
| $k_{d2}$ ($s^{-1}$) | 2.05 | 0.00289 |

What is claimed is:

1. A fusion protein comprising an herpesvirus entry mediator (HVEM) protein and an Fc protein, wherein the HVEM protein comprises an extracellular domain and wherein the HVEM protein comprises at least one amino acid mutation selected from the group consisting of an amino acid mutation at residues 58, 68, 70, and 90 of SEQ ID NO:2, wherein the at least one amino acid mutation is selected from S58R, S58K, S58Q, G68T, L70D, L70E, L70N, L70W, and L90A of SEQ ID NO: 2.

2. A fusion protein comprising an herpesvirus entry mediator (HVEM) protein and an Fc protein, wherein the HVEM protein comprises an extracellular domain and wherein the HVEM protein comprises at least one amino acid mutation selected from the group consisting of an amino acid mutation at residues 58, 68, 70, and 90 of SEQ ID NO:2, wherein the at least one amino acid mutation is selected from the group consisting of:

a) S58R;
b) S58K;
c) S58Q;
d) L70D;
e) L70E;
f) L70N;
g) L90A;
h) S58R and L90A;
i) S58R and G68T;
j) S58R and L70W;
k) S58R, L70D and L90A;
l) S58R, G68T and L90A;
m) S58R, L70W and L90A;
n) S58R, G68T, L70D and L90A; and
o) S58R, G68T, L70W and L90A of SEQ ID NO: 2.

3. The fusion protein of claim 2, wherein the at least one amino acid mutation comprises S58R, G68T, L70W and L90A of SEQ ID NO: 2.

4. A pharmaceutical composition comprising: (a) a fusion protein comprising a non-naturally occurring herpesvirus entry mediator (HVEM) protein and an Fc protein; and (b) a pharmaceutically acceptable carrier, wherein the HVEM protein comprises an extracellular domain and at least one amino acid mutation selected from the group consisting of an amino acid mutation at residues 58, 68, 70, and 90 of SEQ ID NO: 2, wherein the at least one mutation in the HVEM protein is selected from the group consisting of:

a) S58R;
b) S58K;
c) S58Q;
d) L70D;
e) L70E;
f) L70N;
g) L90A;
h) S58R and L90A;
i) S58R and G68T;
j) S58R and L70W;
k) S58R, L70D and L90A;
l) S58R, G68T and L90A;
m) S58R, L70W and L90A;
n) S58R, G68T, L70D and L90A; and
o) S58R, G68T, L70W and L90A of SEQ ID NO: 2.

5. A herpesvirus entry mediator (HVEM) protein comprising mutations S58R, G68T, L70W and L90A of SEQ ID NO: 2.

* * * * *

SEQUENCE LISTING

<160> NUMBER OF SEQ ID NOS: 95

<210> SEQ ID NO 1
<211> LENGTH: 1049
<212> TYPE: DNA
<213> ORGANISM: Homo sapiens
<220> FEATURE:
<223> OTHER INFORMATION: HVEM

<400> SEQUENCE: 1

```
gccgcagcaa tggcgctgag ttcctctgct ggagttcatc ctgctagctg ggttcccgag    60
ctgccggtct gagcctgagg catggagcct cctggagact gggggcctcc tccctggaga   120
tccacccca gaaccgacgt cttgaggctg gtgctgtatc tcaccttcct gggagccccc   180
tgctacgccc cagctctgcc gtcctgcaag gaggacgagt acccagtggg ctccgagtgc   240
tgccccaagt gcagtccagg ttatcgtgtg aaggaggcct gcggggagct gacgggcaca   300
gtgtgtgaac cctgccctcc aggcacctac attgcccacc tcaatggcct aagcaagtgt   360
ctgcagtgcc aaatgtgtga cccagccatg ggcctgcgcg cgagccggaa ctgctccagg   420
acagagaacg ccgtgtgtgg ctgcagccca ggccacttct gcatcgtcca ggacggggac   480
cactgcgccg cgtgccgcgc ttacgccacc tccagcccgg ccagagggt gcagaaggga   540
ggcaccgaga gtcaggacac cctgtgtcag aactgccccc cggggacctt ctctcccaat   600
gggacccctgg aggaatgtca gcaccagacc aagtgcagct ggctggtgac gaaggccgga   660
gctgggacca gcagctccca ctgggtatgg tggtttctct caggagcct cgtcatcgtc   720
attgtttgct ccacagttgg cctaatcata tgtgtgaaaa gaagaaagcc aagggtgat   780
gtagtcaagg tgatcgtctc cgtccagcgg aaaagacagg aggcagaagg tgaggccaca   840
gtcattgagg ccctgcaggc ccctccggac gtcaccacgg tggccgtgga ggagacaata   900
ccctcattca cgggaggag cccaaaccac tgacccacag actctgcacc ccgacgccag   960
agatacctgg agcgacggct gctgaaagag gctgtccacc tggcgaaacc accggagccc  1020
```
ggaggcttgg gggctccgcc ctgggctgg                                        1049

<210> SEQ ID NO 2
<211> LENGTH: 283
<212> TYPE: PRT
<213> ORGANISM: Homo sapiens

<400> SEQUENCE: 2

Met Glu Pro Pro Gly Asp Trp Gly Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280

<210> SEQ ID NO 3
<211> LENGTH: 32
<212> TYPE: DNA
<213> ORGANISM: Homo sapiens

<400> SEQUENCE: 3
aaacccgaag cagtgcaatt aggaaatcag tg                                    32

<210> SEQ ID NO 4
<211> LENGTH: 32
<212> TYPE: DNA
<213> ORGANISM: Homo sapiens

```
<400> SEQUENCE: 4
taattgcact gcttcgggtt tgcatatttc ag                                    32

<210> SEQ ID NO 5
<211> LENGTH: 35
<212> TYPE: DNA
<213> ORGANISM: Homo sapiens

<400> SEQUENCE: 5
acccgaagaa tatcaattag gaaatcagtg ttgtc                                 35

<210> SEQ ID NO 6
<211> LENGTH: 34
<212> TYPE: DNA
<213> ORGANISM: Homo sapiens

<400> SEQUENCE: 6
ttcctaattg atattcttcg ggtttgcata tttc                                  34

<210> SEQ ID NO 7
<211> LENGTH: 33
<212> TYPE: DNA
<213> ORGANISM: Homo sapiens

<400> SEQUENCE: 7
gaagaagtgc cattaggaaa tcagtgttgt ccc                                   33

<210> SEQ ID NO 8
<211> LENGTH: 36
<212> TYPE: DNA
<213> ORGANISM: Homo sapiens

<400> SEQUENCE: 8
atttcctaat ggcacttctt cgggtttgca tatttc                                36

<210> SEQ ID NO 9
<211> LENGTH: 35
<212> TYPE: DNA
<213> ORGANISM: Homo sapiens

<400> SEQUENCE: 9
gcaattagga agtcagtgtt gtcccccatg taaac                                 35

<210> SEQ ID NO 10
<211> LENGTH: 32
<212> TYPE: DNA
<213> ORGANISM: Homo sapiens

<400> SEQUENCE: 10
acaacactga cttcctaatt gcacttcttc gg                                    32

<210> SEQ ID NO 11
<211> LENGTH: 34
<212> TYPE: DNA
<213> ORGANISM: Homo sapiens

<400> SEQUENCE: 11
ttaggaaatg cgtgttgtcc cccatgtaaa caag                                  34

<210> SEQ ID NO 12
<211> LENGTH: 33
<212> TYPE: DNA
```

<213> ORGANISM: Homo sapiens

<400> SEQUENCE: 12
gggacaacac gcatttccta attgcacttc ttc                              33

<210> SEQ ID NO 13
<211> LENGTH: 34
<212> TYPE: DNA
<213> ORGANISM: Homo sapiens

<400> SEQUENCE: 13
cagtgttgtg ccccatgtaa acaaggatat cgtg                             34

<210> SEQ ID NO 14
<211> LENGTH: 33
<212> TYPE: DNA
<213> ORGANISM: Homo sapiens

<400> SEQUENCE: 14
tttacatggg gcacaacact gatttcctaa ttg                              33

<210> SEQ ID NO 15
<211> LENGTH: 36
<212> TYPE: DNA
<213> ORGANISM: Homo sapiens

<400> SEQUENCE: 15
gtgttgtccc aaatgtaaac aaggatatcg tgttac                           36

<210> SEQ ID NO 16
<211> LENGTH: 36
<212> TYPE: DNA
<213> ORGANISM: Homo sapiens

<400> SEQUENCE: 16
ttgtttacat ttgggacaac actgatttcc taattg                           36

<210> SEQ ID NO 17
<211> LENGTH: 33
<212> TYPE: DNA
<213> ORGANISM: Homo sapiens

<400> SEQUENCE: 17
tcccccatgt tcacaaggat atcgtgttac agg                              33

<210> SEQ ID NO 18
<211> LENGTH: 35
<212> TYPE: DNA
<213> ORGANISM: Homo sapiens

<400> SEQUENCE: 18
atatccttgt gaacatgggg gacaacactg atttc                            35

<210> SEQ ID NO 19
<211> LENGTH: 35
<212> TYPE: DNA
<213> ORGANISM: Homo sapiens

<400> SEQUENCE: 19
tgtaaacaag catatcgtgt tacaggacaa tgtac                            35

<210> SEQ ID NO 20
<211> LENGTH: 36

<212> TYPE: DNA
<213> ORGANISM: Homo sapiens

<400> SEQUENCE: 20
aacacgatat gcttgtttac atgggggaca acactg                                    36

<210> SEQ ID NO 21
<211> LENGTH: 38
<212> TYPE: DNA
<213> ORGANISM: Homo sapiens

<400> SEQUENCE: 21
cccccatgta aacaaggagc tcgtgttaca ggacaatg                                  38

<210> SEQ ID NO 22
<211> LENGTH: 38
<212> TYPE: DNA
<213> ORGANISM: Homo sapiens

<400> SEQUENCE: 22
cattgtcctg taacacgagc tccttgttta catggggg                                  38

<210> SEQ ID NO 23
<211> LENGTH: 38
<212> TYPE: DNA
<213> ORGANISM: Homo sapiens

<400> SEQUENCE: 23
caaggatatg ctgttacagg acaatgtacg caatatac                                  38

<210> SEQ ID NO 24
<211> LENGTH: 33
<212> TYPE: DNA
<213> ORGANISM: Homo sapiens

<400> SEQUENCE: 24
tcctgtaaca gcatatcctt gtttacatgg ggg                                       33

<210> SEQ ID NO 25
<211> LENGTH: 33
<212> TYPE: DNA
<213> ORGANISM: Homo sapiens

<400> SEQUENCE: 25
tatcgtgttg caggacaatg tacgcaatat acg                                       33

<210> SEQ ID NO 26
<211> LENGTH: 36
<212> TYPE: DNA
<213> ORGANISM: Homo sapiens

<400> SEQUENCE: 26
acattgtcct gcaacacgat atccttgttt acatgg                                    36

<210> SEQ ID NO 27
<211> LENGTH: 35
<212> TYPE: DNA
<213> ORGANISM: Homo sapiens

<400> SEQUENCE: 27
cgtgttacag cacaatgtac gcaatatacg agtac                                     35

<210> SEQ ID NO 28

<211> LENGTH: 35
<212> TYPE: DNA
<213> ORGANISM: Homo sapiens

<400> SEQUENCE: 28
cgtacattgt gctgtaacac gatatccttg tttac                        35

<210> SEQ ID NO 29
<211> LENGTH: 45
<212> TYPE: DNA
<213> ORGANISM: Homo sapiens

<400> SEQUENCE: 29
aaacaaggat atcgtgttac aaaacaatgt acgcaatata cgagt            45

<210> SEQ ID NO 30
<211> LENGTH: 45
<212> TYPE: DNA
<213> ORGANISM: Homo sapiens

<400> SEQUENCE: 30
actcgtatat tgcgtacatt gttttgtaac acgatatcct tgttt            45

<210> SEQ ID NO 31
<211> LENGTH: 35
<212> TYPE: DNA
<213> ORGANISM: Homo sapiens

<400> SEQUENCE: 31
gttacaggag catgtacgca atatacgagt acaac                        35

<210> SEQ ID NO 32
<211> LENGTH: 32
<212> TYPE: DNA
<213> ORGANISM: Homo sapiens

<400> SEQUENCE: 32
tgcgtacatg ctcctgtaac acgatatcct tg                           32

<210> SEQ ID NO 33
<211> LENGTH: 35
<212> TYPE: DNA
<213> ORGANISM: Homo sapiens

<400> SEQUENCE: 33
ggacaatgtg ggcaatatac gagtacaaca tgtac                        35

<210> SEQ ID NO 34
<211> LENGTH: 35
<212> TYPE: DNA
<213> ORGANISM: Homo sapiens

<400> SEQUENCE: 34
cgtatattgc ccacattgtc ctgtaacacg atatc                        35

<210> SEQ ID NO 35
<211> LENGTH: 34
<212> TYPE: DNA
<213> ORGANISM: Homo sapiens

<400> SEQUENCE: 35
caatgtacgg catatacgag tacaacatgt acag                         34

```
<210> SEQ ID NO 36
<211> LENGTH: 38
<212> TYPE: DNA
<213> ORGANISM: Homo sapiens

<400> SEQUENCE: 36
actcgtatat gccgtacatt gtcctgtaac acgatatc                              38

<210> SEQ ID NO 37
<211> LENGTH: 35
<212> TYPE: DNA
<213> ORGANISM: Homo sapiens

<400> SEQUENCE: 37
acgcaatatg cgagtacaac atgtacactt tgccc                                 35

<210> SEQ ID NO 38
<211> LENGTH: 36
<212> TYPE: DNA
<213> ORGANISM: Homo sapiens

<400> SEQUENCE: 38
tgttgtactc gcatattgcg tacattgttc tgtaac                                36

<210> SEQ ID NO 39
<211> LENGTH: 31
<212> TYPE: DNA
<213> ORGANISM: Homo sapiens

<400> SEQUENCE: 39
ctttgccctg ccggtacgta tgtatcaggg c                                     31

<210> SEQ ID NO 40
<211> LENGTH: 32
<212> TYPE: DNA
<213> ORGANISM: Homo sapiens

<400> SEQUENCE: 40
cgtaccggca gggcaaagtg tacatgttgt ac                                    32

<210> SEQ ID NO 41
<211> LENGTH: 34
<212> TYPE: DNA
<213> ORGANISM: Homo sapiens

<400> SEQUENCE: 41
gtatcagggg cttacaattg taccaattgc actg                                  34

<210> SEQ ID NO 42
<211> LENGTH: 35
<212> TYPE: DNA
<213> ORGANISM: Homo sapiens

<400> SEQUENCE: 42
acaattgtaa gcccctgata catacgtacc gttag                                 35

<210> SEQ ID NO 43
<211> LENGTH: 33
<212> TYPE: DNA
<213> ORGANISM: Homo sapiens

<400> SEQUENCE: 43
caattgcact atgtgtaatg acactgaggt tac                                   33
```

<210> SEQ ID NO 44
<211> LENGTH: 33
<212> TYPE: DNA
<213> ORGANISM: Homo sapiens

<400> SEQUENCE: 44
caattgcact atgtgtaatg acactgaggt tac                33

<210> SEQ ID NO 45
<211> LENGTH: 35
<212> TYPE: DNA
<213> ORGANISM: Homo sapiens

<400> SEQUENCE: 45
ttttccgttg caggcgtcca acatcacaag caacg              35

<210> SEQ ID NO 46
<211> LENGTH: 34
<212> TYPE: DNA
<213> ORGANISM: Homo sapiens

<400> SEQUENCE: 46
ttggacgcct gcaacggaaa atgacgtata attc               34

<210> SEQ ID NO 47
<211> LENGTH: 31
<212> TYPE: DNA
<213> ORGANISM: Homo sapiens

<400> SEQUENCE: 47
caagtgcagt tcaggttatc gtgtgaagga g                  31

<210> SEQ ID NO 48
<211> LENGTH: 30
<212> TYPE: DNA
<213> ORGANISM: Homo sapiens

<400> SEQUENCE: 48
cgataacctg aactgcactt ggggcagcac                    30

<210> SEQ ID NO 49
<211> LENGTH: 32
<212> TYPE: DNA
<213> ORGANISM: Homo sapiens

<400> SEQUENCE: 49
tgcagtccag attatcgtgt gaaggaggcc tg                 32

<210> SEQ ID NO 50
<211> LENGTH: 28
<212> TYPE: DNA
<213> ORGANISM: Homo sapiens

<400> SEQUENCE: 50
acacgataat ctggactgca cttggggc                      28

<210> SEQ ID NO 51
<211> LENGTH: 29
<212> TYPE: DNA
<213> ORGANISM: Homo sapiens

<400> SEQUENCE: 51
gtccaggttg tcgtgtgaag gaggcctgc                     29

<210> SEQ ID NO 52
<211> LENGTH: 30
<212> TYPE: DNA
<213> ORGANISM: Homo sapiens

<400> SEQUENCE: 52
cttcacacga caacctggac tgcacttggg                             30

<210> SEQ ID NO 53
<211> LENGTH: 28
<212> TYPE: DNA
<213> ORGANISM: Homo sapiens

<400> SEQUENCE: 53
gctgacggac acagtgtgtg aaccctgc                              28

<210> SEQ ID NO 54
<211> LENGTH: 28
<212> TYPE: DNA
<213> ORGANISM: Homo sapiens

<400> SEQUENCE: 54
acacactgtg tccgtcagct ccccgcag                              28

<210> SEQ ID NO 55
<211> LENGTH: 29
<212> TYPE: DNA
<213> ORGANISM: Homo sapiens

<400> SEQUENCE: 55
tccaggcccc tacattgccc acctcaatg                             29

<210> SEQ ID NO 56
<211> LENGTH: 27
<212> TYPE: DNA
<213> ORGANISM: Homo sapiens

<400> SEQUENCE: 56
aatgtagggg cctggagggc agggttc                               27

<210> SEQ ID NO 57
<211> LENGTH: 33
<212> TYPE: DNA
<213> ORGANISM: Homo sapiens

<400> SEQUENCE: 57
ctcaatggcc taataagcaa gtgtctgcag tgc                        33

<210> SEQ ID NO 58
<211> LENGTH: 33
<212> TYPE: DNA
<213> ORGANISM: Homo sapiens

<400> SEQUENCE: 58
cacttgctta ttaggccatt gaggtgggca atg                        33

<210> SEQ ID NO 59
<211> LENGTH: 26
<212> TYPE: DNA
<213> ORGANISM: Homo sapiens

<400> SEQUENCE: 59

```
gtgacccacc catgggcctg cgcgcg                                          26

<210> SEQ ID NO 60
<211> LENGTH: 31
<212> TYPE: DNA
<213> ORGANISM: Homo sapiens

<400> SEQUENCE: 60
ggcccatggg tgggtcacac atttggcact g                                    31

<210> SEQ ID NO 61
<211> LENGTH: 28
<212> TYPE: DNA
<213> ORGANISM: Homo sapiens

<400> SEQUENCE: 61
cgcgagctgg aactgctcca ggacagag                                        28

<210> SEQ ID NO 62
<211> LENGTH: 27
<212> TYPE: DNA
<213> ORGANISM: Homo sapiens

<400> SEQUENCE: 62
gagcagttcc agctcgcgcg caggccc                                         27

<210> SEQ ID NO 63
<211> LENGTH: 43
<212> TYPE: DNA
<213> ORGANISM: Homo sapiens

<400> SEQUENCE: 63
catgtgatgt agcgctttat ataaagagac aatctgaaca ctc                       43

<210> SEQ ID NO 64
<211> LENGTH: 39
<212> TYPE: DNA
<213> ORGANISM: Homo sapiens

<400> SEQUENCE: 64
ctttatataa agcgctacat cacatgattc tttcccatg                            39

<210> SEQ ID NO 65
<211> LENGTH: 43
<212> TYPE: DNA
<213> ORGANISM: Homo sapiens

<400> SEQUENCE: 65
atgtgatgta cagcattata taaagagaca atctgaacac tcc                       43

<210> SEQ ID NO 66
<211> LENGTH: 41
<212> TYPE: DNA
<213> ORGANISM: Homo sapiens

<400> SEQUENCE: 66
ttgtctcttt atataatgct gtacatcaca tgattctttc c                         41

<210> SEQ ID NO 67
<211> LENGTH: 38
<212> TYPE: DNA
<213> ORGANISM: Homo sapiens

<400> SEQUENCE: 67
```
ctttatataa aggaccaatc tgaacactcc atcttagc                                38

<210> SEQ ID NO 68
<211> LENGTH: 45
<212> TYPE: DNA
<213> ORGANISM: Homo sapiens

<400> SEQUENCE: 68
gtgttcagat tggtccttta tataaagctg tacatcacat gattc                       45

<210> SEQ ID NO 69
<211> LENGTH: 37
<212> TYPE: DNA
<213> ORGANISM: Homo sapiens

<400> SEQUENCE: 69
agagacaatc tgcacactcc atcttagcag gagatcc                                37

<210> SEQ ID NO 70
<211> LENGTH: 41
<212> TYPE: DNA
<213> ORGANISM: Homo sapiens

<400> SEQUENCE: 70
aagatggagt gtggagattg tctctttata taaagctgta c                           41

<210> SEQ ID NO 71
<211> LENGTH: 37
<212> TYPE: DNA
<213> ORGANISM: Homo sapiens

<400> SEQUENCE: 71
ctttgaacta gcatgccctg tgaaatactg tgctaac                                37

<210> SEQ ID NO 72
<211> LENGTH: 38
<212> TYPE: DNA
<213> ORGANISM: Homo sapiens

<400> SEQUENCE: 72
tcacagggca tgctagttca aagggatctc ctgctaag                               38

<210> SEQ ID NO 73
<211> LENGTH: 37
<212> TYPE: DNA
<213> ORGANISM: Homo sapiens

<400> SEQUENCE: 73
gaactagaat gcgctgtgaa atactgtgct aacaggc                                37

<210> SEQ ID NO 74
<211> LENGTH: 35
<212> TYPE: DNA
<213> ORGANISM: Homo sapiens

<400> SEQUENCE: 74
gtatttcaca gcgcattcta gttcaaaggg atctc                                  35

<210> SEQ ID NO 75
<211> LENGTH: 40
<212> TYPE: DNA
<213> ORGANISM: Homo sapiens

<400> SEQUENCE: 75
acaagttggg cggaagagaa gaacatttca tttttcattc         40

<210> SEQ ID NO 76
<211> LENGTH: 42
<212> TYPE: DNA
<213> ORGANISM: Homo sapiens

<400> SEQUENCE: 76
cttctcttcc gcccaacttg tttgtctatc ttcaagtttt ac      42

<210> SEQ ID NO 77
<211> LENGTH: 36
<212> TYPE: DNA
<213> ORGANISM: Homo sapiens

<400> SEQUENCE: 77
tgttctgcaa attttcagtc taatctcatt gaaagc             36

<210> SEQ ID NO 78
<211> LENGTH: 37
<212> TYPE: DNA
<213> ORGANISM: Homo sapiens

<400> SEQUENCE: 78
gattagactg aaaatttgca gaacagcggt atgaccc            37

<210> SEQ ID NO 79
<211> LENGTH: 38
<212> TYPE: DNA
<213> ORGANISM: Homo sapiens

<400> SEQUENCE: 79
gctgttctgc attttttcag tctaatctca ttgaaagc           38

<210> SEQ ID NO 80
<211> LENGTH: 32
<212> TYPE: DNA
<213> ORGANISM: Homo sapiens

<400> SEQUENCE: 80
tagactgaaa aaatgcagaa cagcggtatg ac                 32

<210> SEQ ID NO 81
<211> LENGTH: 38
<212> TYPE: DNA
<213> ORGANISM: Homo sapiens

<400> SEQUENCE: 81
gttctgcaaa tgctcagtct aatctcattg aaagccac           38

<210> SEQ ID NO 82
<211> LENGTH: 35
<212> TYPE: DNA
<213> ORGANISM: Homo sapiens

<400> SEQUENCE: 82
gagattagac tgagcatttg cagaacagcg gtatg              35

<210> SEQ ID NO 83
<211> LENGTH: 37
<212> TYPE: DNA
<213> ORGANISM: Homo sapiens

```
<400> SEQUENCE: 83
caaattttca gcataatctc attgaaagcc actcaac                               37

<210> SEQ ID NO 84
<211> LENGTH: 34
<212> TYPE: DNA
<213> ORGANISM: Homo sapiens

<400> SEQUENCE: 84
caatgagatt atgctgaaaa tttgcagaac agcg                                  34

<210> SEQ ID NO 85
<211> LENGTH: 38
<212> TYPE: DNA
<213> ORGANISM: Homo sapiens

<400> SEQUENCE: 85
cattgaaagc gactcaacaa ctctttatgt gacagatg                              38

<210> SEQ ID NO 86
<211> LENGTH: 40
<212> TYPE: DNA
<213> ORGANISM: Homo sapiens

<400> SEQUENCE: 86
gttgttgagt cgctttcaat gagattagac tgaaaatttg                            40

<210> SEQ ID NO 87
<211> LENGTH: 42
<212> TYPE: DNA
<213> ORGANISM: Homo sapiens

<400> SEQUENCE: 87
tgaaagccac catacaactc tttatgtgac agatgtaaaa ag                         42

<210> SEQ ID NO 88
<211> LENGTH: 36
<212> TYPE: DNA
<213> ORGANISM: Homo sapiens

<400> SEQUENCE: 88
aagagttgta tggtggcttt caatgagatt agactg                                36

<210> SEQ ID NO 89
<211> LENGTH: 78
<212> TYPE: PRT
<213> ORGANISM: Homo sapiens

<400> SEQUENCE: 89

Cys Lys Glu Asp Glu Tyr Pro Val Gly Ser Glu Cys Cys Pro Lys Cys
1               5                   10                  15

Ser Pro Gly Tyr Arg Val Lys Glu Ala Cys Gly Glu Leu Thr Gly Thr
            20                  25                  30

Val Cys Glu Pro Cys Pro Pro Gly Thr Tyr Ile Ala His Leu Asn Gly
        35                  40                  45

Leu Ser Lys Cys Leu Gln Cys Gln Met Cys Ser Pro Ala Met Gly Leu
    50                  55                  60

Arg Ala Ser Arg Asn Cys Ser Arg Thr Glu Asn Ala Val Cys
65                  70                  75
```

<210> SEQ ID NO 90
<211> LENGTH: 71
<212> TYPE: PRT
<213> ORGANISM: Homo sapiens

<400> SEQUENCE: 90

Cys Lys Pro Glu Glu Val Gln Gly Asn Cys Cys Pro Cys Lys Gln
1               5                   10                  15
Gly Tyr Arg Val Thr Gly Gln Cys Thr Gln Tyr Thr Ala Thr Thr Cys
            20                  25                  30
Thr Leu Cys Pro Asn Gly Thr Tyr Val Ser Gly Leu Tyr Asn Cys Thr
        35                  40                  45
Asn Cys Thr Glu Cys Asn Asp Thr Glu Val Thr Ile Arg Asn Cys Thr
    50                  55                  60
Ser Thr Asn Asn Thr Val Cys
65                  70

<210> SEQ ID NO 91
<211> LENGTH: 74
<212> TYPE: PRT
<213> ORGANISM: Homo sapiens

<400> SEQUENCE: 91

Cys Lys Gln Asp Glu Tyr Ala Val Gly Ser Glu Cys Cys Pro Lys Cys
1               5                   10                  15
Gly Lys Gly Tyr Arg Val Lys Thr Asn Cys Ser Glu Thr Thr Gly Thr
            20                  25                  30
Val Cys Glu Pro Cys Pro Ala Gly Ser Tyr Asn Asp Leu Arg Glu Thr
        35                  40                  45
Ile Cys Thr Gln Cys Asp Thr Cys Asn Ser Ser Ile Ala Val Asn
    50                  55                  60
Arg Cys Asn Thr Thr His Asn Val Arg Cys
65                  70

<210> SEQ ID NO 92
<211> LENGTH: 78
<212> TYPE: PRT
<213> ORGANISM: Homo sapiens

<400> SEQUENCE: 92

Cys Lys Glu Asp Glu Tyr Pro Val Gly Ser Glu Cys Cys Pro Lys Cys
1               5                   10                  15
Ser Pro Gly Tyr Arg Val Lys Glu Ala Cys Gly Glu Leu Thr Gly Thr
            20                  25                  30
Val Cys Glu Pro Cys Pro Pro Gly Thr Tyr Ile Ala His Leu Asn Gly
        35                  40                  45
Leu Ser Lys Cys Leu Gln Cys Gln Met Cys Asp Pro Ala Met Gly Leu
    50                  55                  60
Arg Ala Ser Arg Asn Cys Ser Arg Thr Glu Asn Ala Val Cys
65                  70                  75

<210> SEQ ID NO 93
<211> LENGTH: 73
<212> TYPE: PRT
<213> ORGANISM: Human betaherpesvirus 5

<400> SEQUENCE: 93

Cys Lys Pro Glu Glu Val Gln Leu Gly Asn Gln Cys Cys Pro Pro Cys
1               5                   10                  15

```
Lys Gln Gly Tyr Arg Val Thr Gly Gln Cys Thr Gln Tyr Thr Ser Thr
            20                  25                  30

Thr Cys Thr Leu Cys Pro Asn Gly Thr Tyr Val Ser Gly Leu Tyr Asn
        35                  40                  45

Cys Thr Asn Cys Thr Glu Cys Asn Asp Thr Glu Val Thr Ile Arg Asn
    50                  55                  60

Cys Thr Ser Thr Asn Asn Thr Val Cys
65                  70
```

<210> SEQ ID NO 94
<211> LENGTH: 74
<212> TYPE: PRT
<213> ORGANISM: Macacine betaherpesvirus 3

<400> SEQUENCE: 94

```
Cys Lys Gln Asp Glu Tyr Ala Val Gly Ser Glu Cys Cys Pro Lys Cys
1               5                   10                  15

Gly Lys Gly Tyr Arg Val Lys Thr Asn Cys Ser Glu Thr Thr Gly Thr
            20                  25                  30

Val Cys Glu Pro Cys Pro Ala Gly Ser Tyr Asn Asp Lys Arg Glu Thr
        35                  40                  45

Ile Cys Thr Gln Cys Asp Thr Cys Asn Ser Ser Ser Ile Ala Val Asn
    50                  55                  60

Arg Cys Asn Thr Thr His Asn Val Arg Cys
65                  70
```

<210> SEQ ID NO 95
<211> LENGTH: 76
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Glu, Pro or Gln
<220> FEATURE:
<221> NAME/KEY: MOD_RES
<222> LOCATION: (7)..(7)
<223> OTHER INFORMATION: Pro, Gln or Ala
<220> FEATURE:
<221> NAME/KEY: MOD_RES
<222> LOCATION: (17)..(17)
<223> OTHER INFORMATION: Ser, Lys or Gly
<220> FEATURE:
<221> NAME/KEY: MOD_RES
<222> LOCATION: (18)..(18)
<223> OTHER INFORMATION: Pro, Gln or Lys
<220> FEATURE:
<221> NAME/KEY: MOD_RES
<222> LOCATION: (24)..(24)
<223> OTHER INFORMATION: Glu, Gly or Thr
<220> FEATURE:
<221> NAME/KEY: MOD_RES
<222> LOCATION: (25)..(25)
<223> OTHER INFORMATION: Ala, Gln or Asn
<220> FEATURE:
<221> NAME/KEY: MOD_RES
<222> LOCATION: (27)..(27)
<223> OTHER INFORMATION: Gly, Thr or Ser
<220> FEATURE:
<221> NAME/KEY: MOD_RES
<222> LOCATION: (29)..(29)
<223> OTHER INFORMATION: Leu, Tyr or Thr
<220> FEATURE:
<221> NAME/KEY: MOD_RES
<222> LOCATION: (39)..(39)
<223> OTHER INFORMATION: Pro, Asn or Ala

```
<220> FEATURE:
<221> NAME/KEY: MOD_RES
<222> LOCATION: (43)..(43)
<223> OTHER INFORMATION: Ile, Val or Asn
<220> FEATURE:
<221> NAME/KEY: MOD_RES
<222> LOCATION: (44)..(44)
<223> OTHER INFORMATION: Ala, Ser or Asp
<220> FEATURE:
<221> NAME/KEY: MOD_RES
<222> LOCATION: (45)..(45)
<223> OTHER INFORMATION: His, Lys or absent
<220> FEATURE:
<221> NAME/KEY: MOD_RES
<222> LOCATION: (46)..(46)
<223> OTHER INFORMATION: Leu, Arg or absent
<220> FEATURE:
<221> NAME/KEY: MOD_RES
<222> LOCATION: (47)..(47)
<223> OTHER INFORMATION: Asn, Glu or absent
<220> FEATURE:
<221> NAME/KEY: MOD_RES
<222> LOCATION: (50)..(50)
<223> OTHER INFORMATION: Ser, Tyr or absent
<220> FEATURE:
<221> NAME/KEY: MOD_RES
<222> LOCATION: (51)..(51)
<223> OTHER INFORMATION: Lys, Asn or absent
<220> FEATURE:
<221> NAME/KEY: MOD_RES
<222> LOCATION: (56)..(56)
<223> OTHER INFORMATION: Gln, Thr or Asp
<220> FEATURE:
<221> NAME/KEY: MOD_RES
<222> LOCATION: (57)..(57)
<223> OTHER INFORMATION: Met, Glu or Thr
<220> FEATURE:
<221> NAME/KEY: MOD_RES
<222> LOCATION: (60)..(60)
<223> OTHER INFORMATION: Pro, Asp or Ser
<220> FEATURE:
<221> NAME/KEY: MOD_RES
<222> LOCATION: (61)..(61)
<223> OTHER INFORMATION: Ala, Thr or Ser
<220> FEATURE:
<221> NAME/KEY: MOD_RES
<222> LOCATION: (62)..(62)
<223> OTHER INFORMATION: Met, Glu or Ser
<220> FEATURE:
<221> NAME/KEY: MOD_RES
<222> LOCATION: (63)..(63)
<223> OTHER INFORMATION: Arg, Val or Ile
<220> FEATURE:
<221> NAME/KEY: MOD_RES
<222> LOCATION: (65)..(65)
<223> OTHER INFORMATION: Ser, Ile or Val
<220> FEATURE:
<221> NAME/KEY: MOD_RES
<222> LOCATION: (69)..(69)
<223> OTHER INFORMATION: Ser, Thr or Asn
<220> FEATURE:
<221> NAME/KEY: MOD_RES
<222> LOCATION: (70)..(70)
<223> OTHER INFORMATION: Arg, Ser or Thr
<220> FEATURE:
<221> NAME/KEY: MOD_RES
<222> LOCATION: (72)..(72)
<223> OTHER INFORMATION: Glu, Asn or His
<220> FEATURE:
<221> NAME/KEY: MOD_RES
<222> LOCATION: (74)..(74)
<223> OTHER INFORMATION: Ala, Thr or Val

<400> SEQUENCE: 95

Cys Lys Xaa Asp Glu Tyr Xaa Val Gly Ser Glu Cys Cys Pro Lys Cys
1               5                   10                  15

Xaa Xaa Gly Tyr Arg Val Lys Xaa Xaa Cys Xaa Glu Xaa Thr Gly Thr
```

-continued

```
            20                  25                  30

Val Cys Glu Pro Cys Pro Xaa Gly Thr Tyr Xaa Xaa Xaa Xaa Xaa Gly
        35                  40                  45

Leu Xaa Xaa Cys Thr Gln Cys Xaa Xaa Cys Asn Xaa Xaa Xaa Xaa Ala
    50                  55                  60

Xaa Arg Asn Cys Xaa Xaa Thr Xaa Asn Xaa Val Cys
65                  70                  75
```